(12) United States Patent
Suwa et al.

(10) Patent No.: US 8,389,649 B2
(45) Date of Patent: Mar. 5, 2013

(54) SILOXANE-BASED RESIN COMPOSITION

(75) Inventors: Mitsuhito Suwa, Otsu (JP); Hirokazu Iimori, Otsu (JP)

(73) Assignee: Toray Industries, Inc., Tokyo (JP)

( * ) Notice: Subject to any disclaimer, the term of this patent is extended or adjusted under 35 U.S.C. 154(b) by 84 days.

(21) Appl. No.: 12/864,832

(22) PCT Filed: May 27, 2008

(86) PCT No.: PCT/JP2008/059689
§ 371 (c)(1),
(2), (4) Date: Jul. 27, 2010

(87) PCT Pub. No.: WO2009/096050
PCT Pub. Date: Aug. 6, 2009

(65) Prior Publication Data
US 2010/0316953 A1    Dec. 16, 2010

(30) Foreign Application Priority Data
Jan. 28, 2008   (JP) .................................. 2008-015904

(51) Int. Cl.
*C08L 83/08* (2006.01)

(52) U.S. Cl. .............. 525/477; 106/287.11; 106/287.13; 106/287.16; 106/287.17; 106/287.19; 528/34; 528/38; 556/407; 556/413; 556/436

(58) Field of Classification Search ........................ None
See application file for complete search history.

(56) References Cited

U.S. PATENT DOCUMENTS

| 4,213,914 | A | * | 7/1980 | Bargain et al. ................ 556/419 |
| 4,511,701 | A | | 4/1985 | Ryang |
| 4,582,886 | A | | 4/1986 | Ryang |
| 4,595,732 | A | | 6/1986 | Ryang |
| 4,855,378 | A | * | 8/1989 | Pradl et al. ...................... 528/26 |
| 5,061,774 | A | | 10/1991 | Park et al. |
| 2006/0189779 | A1 | | 8/2006 | Allen et al. |
| 2010/0129618 | A1 | | 5/2010 | Suwa |

FOREIGN PATENT DOCUMENTS

| JP | 60-252487 A | 12/1985 |
| JP | 2-501834 A | 6/1990 |
| JP | 4-211427 A | 8/1992 |
| JP | 5-1078 A | 1/1993 |
| JP | 2006-251794 A | 9/2006 |
| JP | 2007-31321 A | 2/2007 |
| JP | 2007-163720 A | 6/2007 |
| WO | WO 02/102812 A1 | 12/2002 |
| WO | WO 2008/065944 A1 | 6/2008 |

OTHER PUBLICATIONS

International Search Report for PCT/JP2008/059689 mailed Aug. 26, 2008.

* cited by examiner

*Primary Examiner* — Marc Zimmer

(74) *Attorney, Agent, or Firm* — Birch, Stewart, Kolasch & Birch, LLP

(57) ABSTRACT

The present invention is a siloxane-based resin composition including a siloxane-based resin and an imidosilane compound having a specific structure. Moreover, the present invention is a siloxane-based resin composition including a siloxane-based resin which is a reactive product to be obtained by hydrolyzing an alkoxysilane compound and an imidosilane compound having a specific structure and then making the resulting hydrolysate undergo a condensation reaction. According to the present invention, it is possible to form a cured film excellent in adhesion.

11 Claims, No Drawings

SILOXANE-BASED RESIN COMPOSITION

TECHNICAL FIELD

The present invention relates to siloxane-based resin compositions.

BACKGROUND ART

In recent years, following the rapid development of digital cameras, mobile phones with a camera, and so on, there have been demanded miniaturization and pixel densification of optical goods including image sensors. Since the miniaturization of an image sensor causes deterioration of sensitivity, various considerations have been made for increasing the efficiency of incident light incorporation. For example, by providing a condenser lens (henceforth, referred to as a microlens) at the outermost part of an image sensor, light is condensed efficiently and thereby the lowering of sensitivity is prevented. Moreover, there has been proposed to inhibit the reflection of light caused by the refractive index difference between an air medium and a microlens by using a curable composition for a microlens antireflection film containing a titanium oxide particle coated with a metal element oxide, a curable compound, and a curing catalyst (see, for example, patent document 1). Furthermore, for the purpose of inhibiting the reflection of light caused by the refractive index difference between a euphotic part and a color filter, between a color filter and a microlens, etc., and planarizing steps of a base, various planarization films with controlled refractive indices have been used. As coating materials for such planarization films, there have been disclosed, for example, a siloxane-based resin composition obtained by hydrolyzing and condensing an alkoxysilane compound in the presence of metal compound particles (see, for example, patent document 2) and a thermal curable resin composition containing a fluorine-containing siloxane polymer having a fluorine-containing silane compound and an epoxy group-containing silane compound as copolymerization components (see, for example, patent document 3).

Such coating materials to be used for planarization film applications are required to have not only a characteristic to completely cover and planarize steps of a base but also sufficient adhesion to the surface of a substrate composed of a base metal or an inorganic substance, the surface of resin, and the surface of a device. It is known that such a material generally contains a silane coupling agent for improving adhesion (see, for example, patent document 4-5). However, addition of the silane coupling agents disclosed in these documents to siloxane-based resin compositions has failed to offer sufficient adhesion.

Patent document 1: JP 2005-283786 A
Patent document 2: JP 2007-246877 A
Patent document 3: JP 2007-119744 A
Patent document 4: JP 2003-43688 A (paragraph 0032)
Patent document 5: JP 2005-49691 A (paragraph 0109)

DISCLOSURE OF THE INVENTION

Problem to be Solved by the Invention

The present invention was made on the basis of the above-mentioned situations and its object is to provide a siloxane-based resin composition from which a cured film excellent in adhesion can be obtained.

Means for Solving the Problem

The present invention is a siloxane-based resin composition comprising (a) a siloxane-based resin and (b) an imidosilane compound represented by the following formula (4). Moreover, the present invention is a siloxane-based resin composition comprising (a) a siloxane-based resin, wherein the siloxane-based resin (a) is (a-2) a reaction product to be obtained by hydrolyzing one or more alkoxysilane compounds each represented by any one of the following formulae (1) to (3) and an imide silane compound represented by the following formula (5) and then making the resulting hydrolysate undergo a condensation reaction:

[Chem. 1]

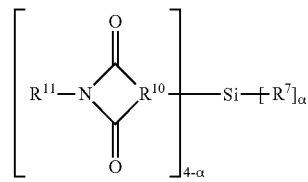

(4)

In formula (4), $R^7$, which may be the same or different, represents an alkyl group having 1 to 6 carbon atoms, an alkoxyl group having 1 to 6 carbon atoms, a phenyl group, a phenoxy group, or a substituted analogue thereof. $R^{10}$, which may be the same or different, represents a trivalent organic group having 3 to 30 carbon atoms. $R^{11}$, which may be the same or different, represents a hydrogen atom or a silicon atom-free monovalent organic group having 1 to 20 carbon atoms. $\alpha$ represents an integer of 1 to 3.

$$R^1Si(OR^2)_3 \quad (1)$$

In formula (1), $R^1$ represents hydrogen, an alkyl group, an alkenyl group, an aryl group, or a substituted analogue thereof. $R^2$, which may be the same or different, represents a methyl group, an ethyl group, a propyl group, an isopropyl group, or a butyl group.

$$R^3R^4Si(OR^5)_2 \quad (2)$$

In formula (2), $R^3$ and $R^4$ each represent hydrogen, an alkyl group, an alkenyl group, an aryl group or a substituted analogue thereof. $R^5$, which may be the same or different, represents a methyl group, an ethyl group, a propyl group, an isopropyl group, or a butyl group.

$$Si(OR^6)_4 \quad (3)$$

In formula (3), $R^6$, which may be the same or different, represents a methyl group, an ethyl group, a propyl group, an isopropyl group, or a butyl group.

[Chem. 2]

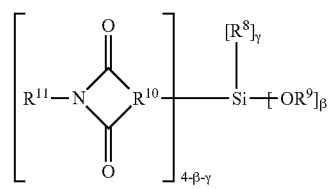

(5)

In formula (5), $R^8$ and $R^9$, which each may be the same or different, each represent a hydrogen atom, an alkyl group having 1 to 6 carbon atoms, a phenyl group, or a substituted analogue thereof. $R^{10}$, which may be the same or different, represents a trivalent organic group having 3 to 30 carbon atoms. $R^{11}$, which may be the same or different, represents a hydrogen atom or a silicon atom-free monovalent organic group having 1 to 20 carbon atoms. β represents an integer of 1 to 3 and γ represents an integer of 0 to 2, provided that β+γ<4.

Effect of the Invention

By the use of the siloxane-based resin composition of the present invention, it is possible to form a cured film excellent in adhesion. A cured film obtained by using the siloxane-based resin composition of the present invention can be used suitably for optical objects, such as an image sensor and an optical filter for a display.

BEST MODE FOR CARRYING OUT THE INVENTION

The siloxane-based resin composition of the present invention is a composition using an imidosilane compound having a specific structure and can be classified into the following two embodiments depending upon the method of introducing the imidosilane compound. A first embodiment is a siloxane-based resin composition comprising (a) a siloxane-based resin and (b) an imidosilane compound represented by the formula (4) given above. By containing the imidosilane compound described later, i.e. component (b), it is possible to greatly improve the adhesion of a cured film to be obtained. A second embodiment is a siloxane-based resin composition comprising a siloxane-based resin which is a reaction product to be obtained by hydrolyzing one or more alkoxysilane compounds each represented by any one of the following formulae (1) to (3) and an imidosilane compound represented by the following formula (5) and then making the resulting hydrolysate undergo a condensation reaction. By synthesizing a siloxane-based resin using the imidosilane compound represented by formula (5), it is possible to introduce a later-described specific structure derived from an imidosilane compound to a siloxane-based resin and it is possible to significantly enhance the adhesion of a cured film to be obtained. The imidosilane compound represented by the following formula (4) or formula (5) serves as an adhesion improving agent. In the present invention, the term "siloxane-based resin" encompasses both a siloxane resin and a particle surface-grafted polysiloxane, which is described later.

First, the siloxane-based resin (a) is described.

In the first embodiment of the siloxane-based resin composition of the present invention, the siloxane-based resin (a) is not particularly restricted if it is a resin which has continuous siloxane bonds as a skeleton. One example is (a-1) a reaction product to be obtained by hydrolyzing one or more alkoxysilane compounds each represented by any one of the following formulae (1) to (3) and then making the resulting hydrolysate undergo a condensation reaction.

$R^1Si(OR^2)_3$ (1)

In formula (1), $R^1$ represents hydrogen, an alkyl group, an alkenyl group, an aryl group, or a substituted analogue thereof. The number of carbon atoms of the alkyl group and the alkenyl group is preferably 1 to 4, and the number of carbon atoms of the aryl group is preferably 6 to 14. Examples of the substituent to be introduced into the substituted analogue include halogen-containing groups, epoxy-containing groups, amino-containing groups, (meth) acryloyl-containing groups, cyano-containing groups, fluorene-containing groups, and a vinyl group. $R^2$, which may be the same or different, represents a methyl group, an ethyl group, a propyl group, an isopropyl group, or a butyl group. The butyl group is preferably a n-butyl group.

$R^3R^4Si(OR^5)_2$ (2)

In formula (2), $R^3$ and $R^4$ each represent hydrogen, an alkyl group, an alkenyl group, an aryl group or a substituted analogue thereof. The number of carbon atoms of the alkyl group and the alkenyl group is preferably 1 to 4, and the number of carbon atoms of the aryl group is preferably 6 to 14. Examples of the substituent to be introduced into the substituted analogue include halogen-containing groups, epoxy-containing groups, amino-containing groups, (meth) acryloyl-containing groups, and a vinyl group. $R^5$, which may be the same or different, represents a methyl group, an ethyl group, a propyl group, an isopropyl group, or a butyl group. The butyl group is preferably a n-butyl group.

$Si(OR^6)_4$ (3)

In formula (3), $R^6$, which may be the same or different, represents a methyl group, an ethyl group, a propyl group, an isopropyl group, or a butyl group. A methyl group or an ethyl group is preferable.

Examples of the trifunctional alkoxysilane compound represented by formula (1) include methyltrimethoxysilane, methyltriethoxysilane, methyltripropoxysilane, methyltriisopropoxysilane, methyltributoxysilane, ethyl trimethoxysilane, ethyltriethoxysilane, hexyltrimethoxysilane, octadecyltrimethoxysilane, octadecyltriethoxysilane, phenyltrimethoxysilane, phenyltriethoxysilane, phenyltriisopropoxysilane, naphthyltrimethoxysilane, naphthyltriethoxysilane, naphthyltriisopropoxysilane, anthracenyltrimethoxysilane, anthracenyltriethoxysilane, anthracenyltriisopropoxysilane, phenanthryltrimethoxysilane, phenanthryltriethoxysilane, phenanthryltriisopropoxysilane, biphenyltrimethoxysilane, biphenyltriethoxysilane, biphenyltriisopropoxysilane, fluorenyltrimethoxysilane, fluorenyltriethoxysilane, fluorenyltriisopropoxysilane, 3-aminopropyltriethoxysilane, N-(2-aminoethyl)-3-aminopropyltrimethoxysilane, 3-chloropropyltrimethoxysilane, 3-(N,N-diglycidyl)aminopropyltrimethoxysilane, 3-glycidoxypropyltrimethoxysilane, vinyltrimethoxysilane, vinyltriethoxysilane, γ-methacryloxypropyltrimethoxysilane, γ-methacryloxypropyltriethoxysilane, γ-aminopropyltrimethoxysilane, γ-aminopropyltriethoxysilane, N-β-(aminoethyl)-γ-aminopropyltrimethoxysilane, β-cyanoethyltriethoxysilane, glycidoxymethyltrimethoxysilane, glycidoxymethyltriethoxysilane, α-glycidoxyethyltrimethoxysilane, α-glycidoxymethyltriethoxysilane, β-glycidoxyethyltrimethoxysilane, β-glycidoxyethyltriethoxysilane, α-glycidoxypropyltrimethoxysilane, α-glycidoxypropyltriethoxysilane, β-glycidoxypropyltrimethoxysilane, β-glycidoxypropyltriethoxysilane, γ-glycidoxypropyltrimethoxysilane, γ-glycidoxypropyltriethoxysilane, γ-glycidoxypropyltripropoxysilane, γ-glycidoxypropyltriisopropoxysilane, γ-glycidoxypropyltributoxysilane, α-glycidoxybutyltrimethoxysilane, α-glycidoxybutyltriethoxysilane, β-glycidoxybutyltrimethoxysilane, β-glycidoxybutyltriethoxysilane, γ-glycidoxybutyltrimethoxysilane, γ-glycidoxybutyltriethoxysilane, δ-glycidoxybutyltrimethoxysilane, δ-glycidoxybutyltriethoxysilane, (3,4-epoxycyclohexyl)methyltrimethoxysilane, (3,4-epoxycyclohexyl)methyltriethoxysilane, 2-(3,4-epoxycyclohexyl)ethyltripropoxysilane, 2-(3,4-epoxycyclohexyl)ethyltributoxysilane, 2-(3,4- epoxycyclohexyl)ethyltrimethoxysilane, 2-(3,4-epoxycyclohexyl)ethyltriethoxysilane, 3-(3,4-epoxycyclohexyl)propyltrimethoxysilane, 3-(3,4-epoxycyclohexyl)propyltriethoxysilane, 4-(3,4-epoxycyclohexyl)butyltrimethoxysilane, 4-(3,4-epoxycyclohexyl)butyltriethoxysilane, trifluoromethyltrimethoxysilane, trifluoromethyltrimethoxysilane, trifluoropropyltrimethoxysilane, trifluoropropyltriethoxysilane, perfluoropropylethyltrimethoxysilane, perfluoropropylethyltriethoxysilane, perfluoropentylethyltrimethoxysilane, perfluoropentylethyltriethoxysilane, tridecafluorooctyltrimethoxysilane, tridecafluorooctyltriethoxysilane, tridecafluorooctyltripropoxysilane, tridecafluorooctyltriisopropoxysilane, heptadecafluorodecyltrimethoxysilane, and heptadecafluorodecyltriethoxysilane.

Among these, methyltrimethoxysilane, methyltriethoxysilane, phenyltrimethoxysilane, and phenyltriethoxysilane are preferable from the viewpoint of the crack resistance of a cured film to be obtained.

Examples of the bifunctional alkoxysilane compound represented by formula (2) include dimethyldimethoxysilane, dimethyldiethoxysilane, diphenyldimethoxysilane, diphenyldiethoxysilane, methylphenyldimethoxysilane, methylvinyldimethoxysilane, methylvinyldiethoxysilane, γ-glycidoxypropylmethyldimethoxysilane, γ-aminopropylmethyldimethoxysilane, γ-aminopropylmethyldiethoxysilane, N-(2-aminoethyl)-3-aminopropylmethyldimethoxysilane, γ-methacryloxypropylmethyldimethoxysilane, γ-methacryloxypropylmethyldiethoxysilane, glycidoxymethyldimethoxysilane, glycidoxymethylmethyldiethoxysilane, α-glycidoxyethylmethyldimethoxysilane, α-glycidoxethylmethyldiethoxysilane, β-glycidoxyethylmethyldimethoxysilane, β-glycidoxyethylmethyldiethoxysilane, α-glycidoxypropylmethyldimethoxysilane, α-glycidoxypropylmethyldiethoxysilane, β-glycidoxypropylmethyldimethoxysilane, β-glycidoxypropylmethyldiethoxysilane, γ-glycidoxypropylmethyldimethoxysilane, γ-glycidoxypropylmethyldiethoxysilane, γ-glycidoxypropylmethyldipropoxysilane, β-glycidoxypropylmethyldibutoxysilane, γ-glycidoxypropylmethyldi(methoxyethoxy)silane, γ-glycidoxypropylethyldimethoxysilane, γ-glycidoxypropylethyldiethoxysilane, γ-glycidoxypropylvinyldimethoxysilane, γ-glycidoxypropylvinyldiethoxysilane, trifluoropropylmethyldimethoxysilane, trifluoropropylmethyldiethoxysilane, trifluoropropylethyldimethoxysilane, trifluoropropylethyldiethoxysilane, trifluoropropylvinyldimethoxysilane, trifluoropropylvinyldiethoxysilane, heptadecafluorodecylmethyldimethoxysilane, 3-chloropropylmethyldimethoxysilane, 3-chloropropylmethyldiethoxysilane, cyclohexylmethyldimethoxysilane, and octadecylmethyldimethoxysilane.

Among these, dimethyldialkoxysilanes are used preferably for the purpose of imparting flexibility to a cured film to be obtained.

Examples of the tetrafunctional alkoxysilane compound represented by formula (3) include tetramethoxysilane and tetraethoxysilane.

As to the alkoxysilane compound represented by any one of these formulae (1) to (3), it is permitted to use either a single compound alone or two or more compounds in combination.

Next, in the second embodiment of the siloxane-based resin composition of the present invention, the siloxane-based resin (a) is (a-2) a reaction product to be obtained by hydrolyzing one or more alkoxysilane compounds each represented by any one of the formulae (1) to (3) given above and an imidosilane compound represented by the following formula (5) and then making the resulting hydrolysate undergo a condensation reaction. As to the alkoxysilane compound and the imidosilane compound, two or more compounds may be used in combination.

[Chem. 3]

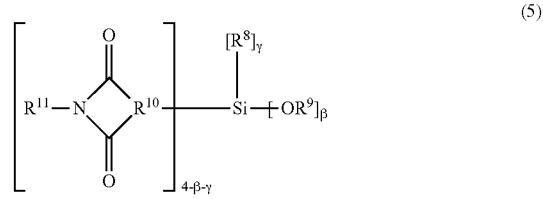

In formula (5), $R^8$ and $R^9$, which each may be the same or different, each represent a hydrogen atom, an alkyl group having 1 to 6 carbon atoms, a phenyl group, or a substituted analogue thereof. $R^{10}$, which may be the same or different, represents a trivalent organic group having 3 to 30 carbon atoms. $R^{11}$, which may be the same or different, represents a hydrogen atom or a silicon atom-free monovalent organic group having 1 to 20 carbon atoms. β represents an integer of 1 to 3 and γ represents an integer of 0 to 2, provided that β+γ<4.

By synthesizing the reaction product (a-2) by using the imidosilane compound represented by formula (5), it is possible to greatly improve the adhesion of a cured film to be obtained. The imidosilane compound represented by formula (5) has an imide moiety excellent in solvent resistance, adhesion, and softness. An Si—$[OR^9]_β$ portion of the imidosilane compound is incorporated into the reaction product through the hydrolysis and condensation reaction with the alkoxysilane compound represented by any one of the formulas (1) to (3). Thereby the flexibility and solvent resistance of a cured film is improved. Furthermore, since the imidosilane compound is incorporated into a siloxane skeleton by an Si—$[OR^9]_β$ portion, it is thought that the nitrogen atom in an imido group points to the outside (the side of a substrate in a constitution having the cured film on the substrate) in the cured film. Therefore, it is thought that a lone electron pair of a nitrogen atom and a hydroxyl group, which is generally present on the substrate such as silicon, efficiently do an interaction, such as hydrogen bonding, and, as a result, the adhesion increases. Moreover, since an imide moiety is inhibited from cure shrinkage more in comparison to a compound having an amide acid structure which forms a ring with heat, the siloxane-based resin composition of the present invention has excellent planarization characteristics.

Specific example of $R^8$ and $R^9$ in formula (5) given above include a hydrogen atom, a methyl group, an ethyl group, a n-propyl group, an isopropyl group, and a phenyl group. Moreover, examples of substituted analogues thereof include alkoxyalkyl groups, alkylphenyl groups, and alkoxyphenyl groups.

From the viewpoint of the reactivity with an alkoxysilane compound represented by any one of formulae (1) to (3), γ is preferably 0. Moreover, from the viewpoint of adhesion, it is preferable that β+γ≦2.

In formula (5) given above, $R^{10}$, which may be the same or different, represents a trivalent organic group having 3 to 30 carbon atoms and is a residual group of an acid anhydride in the acid anhydride-containing silane compound. The acid anhydride which constitutes $R^{10}$ preferably contains an aromatic ring or an aliphatic ring. Specific examples of such an acid anhydride include maleic anhydride, phthalic anhydride, methylphthalic anhydride, succinic anhydride, glutaric anhydride, 4-methylcyclohexane-1,2-dicarboxylic anhydride, cis-4-cyclohexene-1,2-dicarboxylic anhydride, cis-1,2-cyclohexanedicarboxylic anhydride, 1,8-naphthalic anhydride, methyl-5-norbornene-2,3-dicarboxylic anhydride, 5-norbornene-2,3-dicarboxylic anhydride, 3,4,5,6-tetrahydrophthalic anhydride, "RIKACID (registered trademark)" HNA (commercial name, produced by New Japan Chemical Co., Ltd.), "RIKACID" HNA-100 (commercial name, produced by New Japan Chemical Co., Ltd.), and analogues of these acid anhydrides whose some hydrogen atoms have been substituted with a monovalent organic group having 1 to 10 carbon atoms. Examples of the monovalent organic group having 1 to 10 include alkyl groups, such as a methyl group, an ethyl group, a n-propyl group, a n-butyl group, and a n-pentyl group, oxyalkyl groups, such as an oxymethyl group, an oxyethyl group, an oxy-n-propyl group, an oxy-n-butyl group, and an oxy-n-pentyl group. Among these, a methyl group, an ethyl group, a n-propyl group, and a n-butyl group are preferable because they can be prepared easily. Among these acid anhydrides, phthalic anhydride, succinic anhydride, glutaric anhydride, 4-methylcyclohexane-1,2-dicarboxylic anhydride, 1,8-naphthalic anhydride, 5-norbornene-2,3-dicarboxylic anhydride, methylphthalic anhydride, and compounds resulting from substitution of the foregoing anhydrides with a monovalent organic group having 1 to 10 carbon atoms are preferable. In particular, phthalic anhydride, succinic anhydride, and glutaric anhydride are more preferable from the viewpoint of transparency and adhesion.

In formula (5) given above, $R^{11}$, which may be the same or different, represents a hydrogen atom or a silicon atom-free monovalent organic group having 1 to 20 carbon atoms. Specific examples of the organic group include alkyl groups, such as a methyl group, an ethyl group, a n-propyl group, an isopropyl group, a n-butyl group, a t-butyl group, and a cyclohexyl group, hydroxyalkyl groups, such as a 2-hydroxyethyl group, aryl groups, such as a phenyl group, alkoxyaryl groups, such as a methoxyphenyl group, and alkoxyl groups, such as a methoxy group, an ethoxy group, a n-propoxy group, and an isopropoxy group.

An isopropyl group, a t-butyl group, a cyclohexyl group, a methoxy group, or an ethoxy group is preferable because of the ease of their synthesis. Moreover, from the viewpoint of adhesion, a hydrogen atom, hydroxyalkyl groups, such as a methylol group and an ethylol group, an i-propyl group, a t-butyl group, and a phenyl group, which decompose at the time of curing to generate a hydrogen atom, are preferable. A hydrogen atom, an i-propyl group, and a t-butyl group are more preferable.

Specific examples of the imidosilane compound represented by formula (5) include the compounds provided below and the compounds which will be described later as examples of the imidosilane compound represented by formula (4).

[Chem. 4]

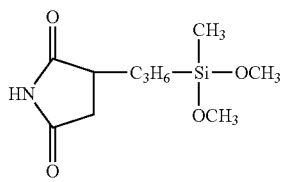

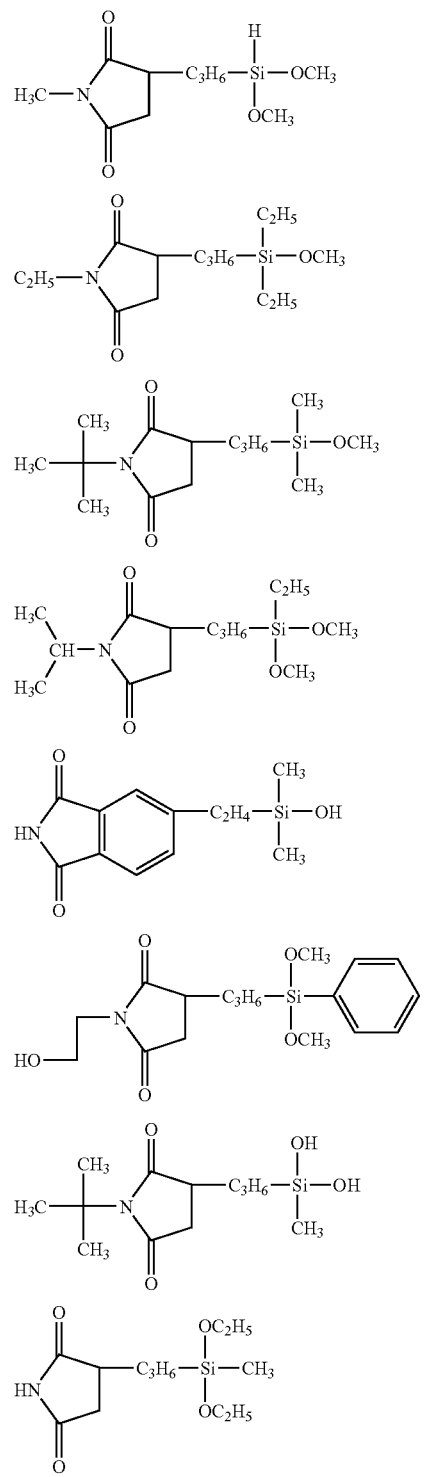

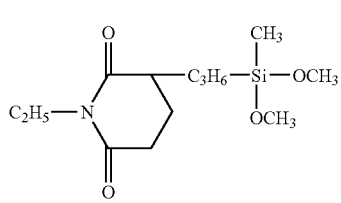

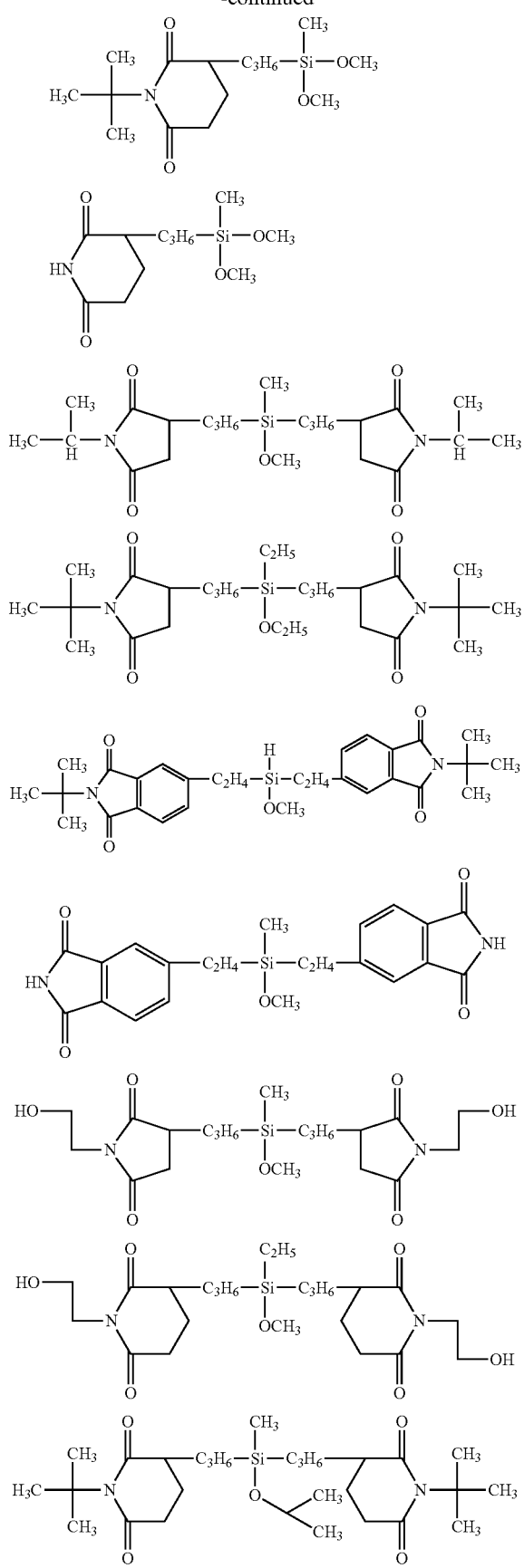
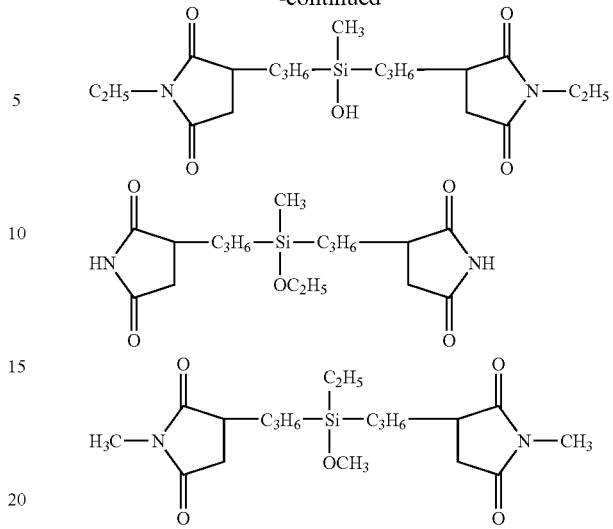

In the present invention, the amount of the imidosilane compound represented by formula (5) to be used for the reaction product (a-2) is preferably 5 parts by weight or more relative to 100 parts by weight of the total amount of the alkoxysilane compound represented by any one of formulae (1) to (3) and the imidosilane compound represented by formula (5); if so, the adhesion and the crack resistance of a cured film increases more. Moreover, it is more preferably 10 parts by weight or more; if so, it is possible to reduce the cure shrinkage ratio and enhance the crack resistance more. On the other hand, it is preferably 50 parts by weight or less; if so, it is possible to keep the transparency of a cured film high.

In the siloxane-based resin composition of the present invention, when the siloxane-based resin (a) is the aforementioned reaction product (a-1), it is preferably a particle surface-grafted polysiloxane, which is a reaction product to be obtained by hydrolyzing one or more alkoxysilane compounds each represented by any one of formulae (1) to (3) given above in the presence of at least one kind of compound particles selected from the group consisting of silicon compound particles, aluminum compound particles, tin compound particles, titanium compound particles, and zirconium compound particles and then making the resulting hydrolysate undergo a condensation reaction. On the other hand, when the siloxane-based resin (a) is the reaction product (a-2), it is preferably particle surface-grafted polysiloxane, which is a reaction product to be obtained by hydrolyzing one or more alkoxysilane compounds each represented by any one of formulae (1) to (3) given above and an imide silane compound represented by formula (5) given above in the presence of at least one kind of compound particles selected from the group consisting of silicon compound particles, aluminum compound particles, tin compound particles, titanium compound particles, and zirconium compound particles and then making the resulting hydrolysate undergo a condensation reaction. By incorporating these compound particles, it is possible to easily adjust the refractive index of a coating film and a cured film to be obtained.

Examples of the compound particles include oxides, sulfides, and hydroxides of silicon, aluminum, tin, titanium, or zirconium. Compound particles may be chosen appropriately depending upon the refractive index of a desired coating film or a desired cured film. For example, in order to make a refractive index fall within the range of 1.60 to 1.80, zirconium oxide particles, tin oxide particles, titanium oxide particles, and composite particles thereof are used preferably. In particular, titanium oxide particles and zirconium oxide particles are preferable because they have a great effect in increasing a refractive index, and titanium oxide particles are more preferable. On the other hand, in order to make a refractive index lower than 1.60, silica particles, aluminum oxide particles, and composite particles thereof are used preferably. Particularly, silica particles are preferable because silica particles can make a refractive index lower. Two or more kinds of such compound particles may be used together. Moreover, in order to make compound particles easier to react with an alkoxysilane compound or an imidosilane compound, compound particles having a group capable of reacting with the alkoxysilane compound or the imidosilane compound, such as a hydroxyl group, on their surface are preferable.

The number average particle diameter of the compound particles is preferably 1 nm or more from the viewpoint of the crack resistance of a cured film to be obtained. Moreover, in use as an embedded material for waveguides, it is preferably 40 nm or less from the viewpoint of embeddability. In order to make the crack resistance of a cured film compatible with the transparency or embeddability of the film, the number average particle diameter is more preferably 1 nm to 30 nm. Here, although the number average particle diameter of compound particles can be measured by a gas absorption method, a dynamic light scattering method, an X-ray small angle scattering method, a method of directly measuring a particle diameter with a transmission electron microscope or a scanning electron microscope, etc., the number average particle diameter in the present invention is a value measured by a dynamic light scattering method.

The content of the compound particles in the siloxane-based resin composition is preferably 5% by weight or more of the reaction product (a-1) or (a-2), and more preferably 10% by weight or more. On the other hand, it is preferably 90% by weight or less, and more preferably 70% by weight or less. If it is within such ranges, it is possible to obtain a cured film that is better in transmittance and crack resistance.

Furthermore, in order to make the cure shrinkage ratio smaller, the content is preferably 20% by weight or more of the reaction product (a-1) or (a-2).

As to examples of the compound particles, examples of commercially available metal compound particles include tin oxide-titanium oxide composite particles, e.g., "Optolake (registered trademark)" TR-502, "Optolake" TR-504, "Optolake" TR-520, and "Optolake" TR-513, silicon oxide-titanium oxide composite particles, e.g., "Optolake" TR-503, "Optolake" TR-527, "Optolake" TR-528, and "Optolake" TR-529, titanium oxide particles, e.g., "Optolake" TR-505 (the above are commercial names, produced by CATALYSTS & CHEMICALS IND. Co., Ltd.), zirconium oxide particles (produced by Kojundo Chemical Lab. Co., Ltd.), tin oxide-zirconium oxide composite particles (produced by CATALYSTS & CHEMICALS IND. Co., Ltd.), and tin oxide particles (produced by Kojundo Chemical Lab. Co., Ltd.). Moreover, examples of the silicon compound particles include IPA-ST having a number average particle diameter of 12 nm, which contains isopropanol as a dispersion medium, MIBK-ST having a number average particle diameter of 12 nm, which contains methy isobutyl ketone as a dispersion medium, PGM-ST having a number average particle diameter of 15 nm, which contains propylene glycol monomethyl ether as a dispersion medium (commercial names, produced by Nissan Chemical Industries, Ltd.) OSCAR 101 having a number average particle diameter of 12 nm, which contains γ-butyrolactone as a dispersion medium, QUATRON PL-2L-PGME having a number average particle diameter of 16 nm, which contains propylene glycol monomethyl ether as a dispersion medium, QUATRON PL-2L-BL having a number average particle diameter of 17 nm, which contains γ-butyrolactone as a dispersion medium, QUATRON PL-2 L-DAA having a number average particle diameter of 17 nm, which contains diacetone alcohol as a dispersion medium, and QUATRON PL-2L, GP-2L having a number average particle diameter of 18 to 20 nm, which contain water as a dispersed solution (commercial names, produced by FUSO CHEMICAL CO., LTD.).

The (a-1) and (a-2) to be used for the present invention are reaction products which are obtained by hydrolyzing the aforementioned alkoxysilane compound and optionally the aforementioned imidosilane compound (henceforth, these are collectively called silane compound(s)) and then making the resulting hydrolysate undergo a condensation reaction. It is preferable to hydrolyze the silane compound(s) in the presence of the above-mentioned compound particles and then make the hydrolysate undergo a condensation reaction.

The hydrolysis reaction is preferably carried out in a solvent by using an acid catalyst. Specifically, it is preferable to add an acid catalyst and water to the silane compound(s) in a solvent over 1 to 180 minutes and then carry out the reaction at room temperature to 110° C. for 1 to 180 minutes. By carrying out a hydrolysis reaction under such conditions, it is possible to inhibit a rapid reaction. The reaction temperature is more preferably 40 to 105° C.

Moreover, it is preferable to obtain a silanol compound by a hydrolysis reaction and then carry out a condensation reaction by heating the reaction solution at a temperature that is not lower than 50° C. and not higher than the boiling point of the solvent for 1 to 100 hours. In order to increase the degree of polymerization of a reaction product, it is also permitted to perform reheating or addition of a base catalyst.

As to conditions of the hydrolysis, it is possible to obtain physical properties suitable for an intended application by determining, for example, an acid concentration, a reaction temperature, and a reaction time in consideration of a reaction scale, the size and the shape of a reaction container, etc.

Examples of the acid catalyst to be used for the hydrolysis reaction include acid catalysts such as hydrochloric acid, acetic acid, formic acid, nitric acid, oxalic acid, sulfuric acid, phosphoric acid, polyphosphoric acid, polycarboxylic acid or its anhydride, and an ion exchange resin. Particularly, an acidic aqueous solution prepared by using formic acid, acetic acid, or phosphoric acid is preferable.

A preferable content of such an acid catalyst is preferably 0.05 parts by weight or more, more preferably 0.1 parts by weight or more and preferably 10 parts by weight or less, and more preferably 5 parts by weight or less relative to 100 parts by weight of all silane compounds to be used in the hydrolysis reaction. Here, the amount of all silane compounds means the collective amount of a silane compound, its hydrolysate, and its condensate, and the same shall apply hereinafter. By determining the amount of the acid catalyst to be 0.05 parts by weight or more, the hydrolysis proceeds smoothly and by determining it to be 10 parts by weight or less, it becomes easy to control the hydrolysis reaction.

The solvent is not particularly restricted and it is appropriately chosen in consideration of the stability, the wettability, the volatility, and so on of the siloxane-based resin composition. It is permitted to use not only one solvent but also two or more solvents. Examples of the solvent include alcohols, such as methanol, ethanol, propanol, isopropanol, butanol, isobutanol, t-butanol, pentanol, 4-methyl-2-pentanol, 3-methyl-2-butanol, 3-methyl-3-methoxy-1-butanol, and diacetone alcohol; glycols, such as ethylene glycol and propylene glycol; ethers, such as ethylene glycol monomethyl ether, ethylene glycol monoethyl ether, propylene glycol monomethyl ether, propylene glycol monoethyl ether, propylene glycol monopropyl ether, propylene glycol monobutyl ether, propylene glycol mono-t-butyl ether, ethylene glycol dimethyl ether, ethylene glycol diethyl ether, diethylene glycol dibutyl ether, and diethyl ether; ketones, such as methyl ethyl ketone, acetylacetone, methyl propyl ketone, methyl butyl ketone, methyl isobutyl ketone, diisobutyl ketone, cyclopentanone, and 2-heptanone; amide, such as dimethylformamide and dimethylacetamide; acetates, such as ethyl acetate, propyl acetate, butyl acetate, isobutyl acetate, ethylene glycol monoethyl ether acetate, propylene glycol monomethyl ether acetate, 3-methoxybutyl acetate, 3-methyl-3-methoxybutyl acetate, methyl lactate, ethyl lactate, and butyl lactate; aromatic or aliphatic hydrocarbons, such as toluene, xylene, hexane, and cyclohexane; γ-butyrolactone, N-methyl-2-pyrrolidone, and dimethyl sulfoxide. Among these, propylene glycol monomethyl ether, propylene glycol monomethyl ether acetate, propylene glycol monoethyl ether, propylene glycol monopropyl ether, propylene glycol monobutyl ether, propylene glycol mono-t-butyl ether, and γ-butyrolactone are used preferably from the viewpoint of the transmittance, the crack resistance, and so on of a cured film. Moreover, it is also preferable to adjust the resin composition to a proper concentration by further adding a solvent after the completion of a hydrolysis reaction. Moreover, it is also permitted to evaporate and remove generated alcohol and the like wholly or partly under heating and/or pressure reduction after hydrolysis and then add an appropriate solvent.

The amount of the solvent to be used in a hydrolysis reaction is preferably 50 parts by weight or more, and more preferably 80 parts by weight or more to 100 parts by weight of the whole silane compound. On the other hand, it is preferably 500 parts by weight or less, and more preferably 200 parts by weight or less. By adjusting the amount of the solvent to 50 parts by weight or more, it is possible to inhibit the generation of gel. By adjusting it to 500 parts by weight or less, the hydrolysis reaction proceeds rapidly.

The water to be used for the hydrolysis reaction is preferably ion exchange water. The amount of the water, which may be chosen optionally, is preferably within the range of 1.0 to 4.0 mol per mol of the silane compound.

Next, the imidosilane compound represented by formula (4) given below (b) is described. In the first embodiment of the siloxane-based resin composition of the present invention, it is possible to greatly improve the adhesion of a cured film to be obtained, by containing such an imidosilane compound. The imidosilane compound represented by formula (4) (b) has an imide moiety excellent in solvent resistance, adhesion, and softness. It is thought that when curing a siloxane-based resin composition, an Si—$[R^7]_\alpha$ portion reacts with a siloxane matrix formed of the siloxane-based resin, which is component (a), so that an imido moiety is incorporated into a cured film by an organic bond. Thereby the flexibility and solvent resistance of a cured film is improved. Furthermore, since the imidosilane compound is incorporated into a siloxane matrix by an Si—$[OR^7]_\alpha$ portion, it is thought that the nitrogen atom in an imido group points to the outside (the side of a substrate in a constitution having the cured film on the substrate) in the cured film. Therefore, it is thought that a lone electron pair of a nitrogen atom and a hydroxyl group, which is generally present on the substrate such as silicon, efficiently do an interaction, such as hydrogen bonding, and, as a result, the adhesion increases. Moreover, since an imide moiety is inhibited from cure shrinkage more in comparison to a compound having an amide acid group which forms a ring with heat, the siloxane-based resin composition of the present invention has excellent planarization characteristics. In the present invention, two or more kinds of the imidosilane compound, which is component (b), may be contained. It is also preferable for the siloxane-based resin composition of the present invention in the second embodiment to contain such a imidosilane compound (b).

[Chem. 5]

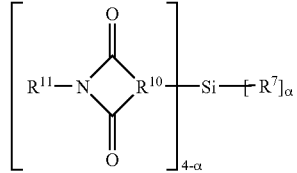

(4)

In formula (4), $R^7$, which may be the same or different, represents an alkyl group having 1 to 6 carbon atoms, an alkoxyl group having 1 to 6 carbon atoms, a phenyl group, a phenoxy group, or a substituted analogue thereof. $R^{10}$, which may be the same or different, represents a trivalent organic group having 3 to 30 carbon atoms. $R^{11}$, which may be the same or different, represents a hydrogen atom or a silicon atom-free monovalent organic group having 1 to 20 carbon atoms. α represents an integer of 1 to 3.

Specific example of the alkyl group of $R^7$ in formula (4) given above include a methyl group, an ethyl group, a n-propyl group, and an isopropyl group. A methyl group or an ethyl group is preferable from the easiness of synthesis. Specific examples of the alkoxyl group include a methoxy group, an ethoxy group, a n-propoxy group, and an isopropoxy group. A methoxy group or an ethoxy group is preferable from the easiness of synthesis. Examples of such substituted analogues, the groups having been provided as examples of the substituted analogues in $R^8$ to $R^9$, alkylphenoxy groups, such as a 4-methylphenoxy group and a 4-ethylphenoxy group, and alkoxyphenoxy groups, such as a 4-methoxyphenoxy group and a 4-ethoxyphenoxy group.

In formula (4) given above, to $R^{18}$ and $R^{11}$ is applied the description having been made with respect to those in formula (5). From the viewpoint of adhesion, it is preferable that α≦2.

As the imidosilane compound represented by formula (4), the compounds shown below can be listed.

[Chem. 6]

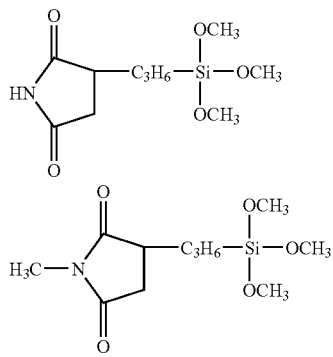

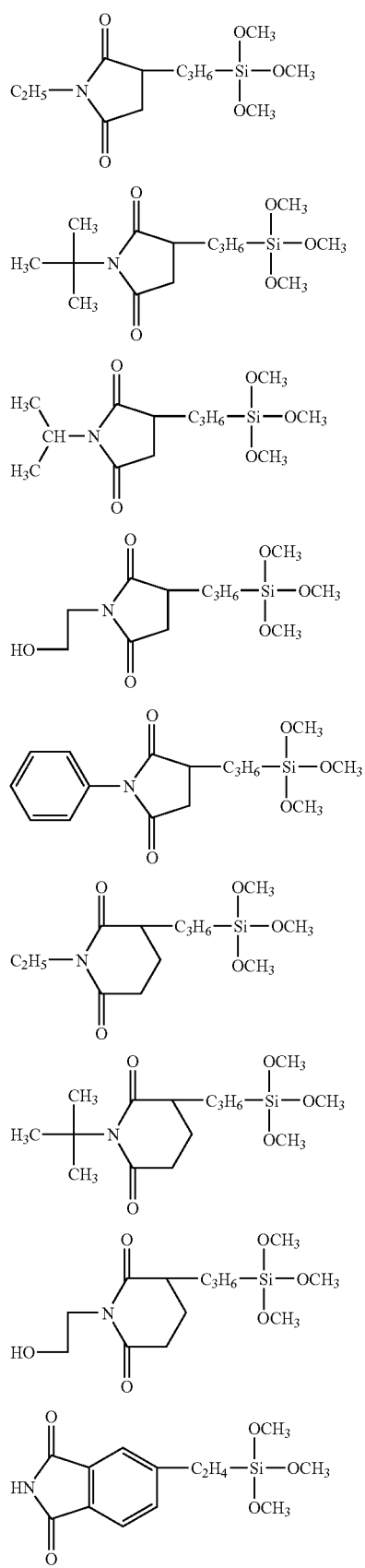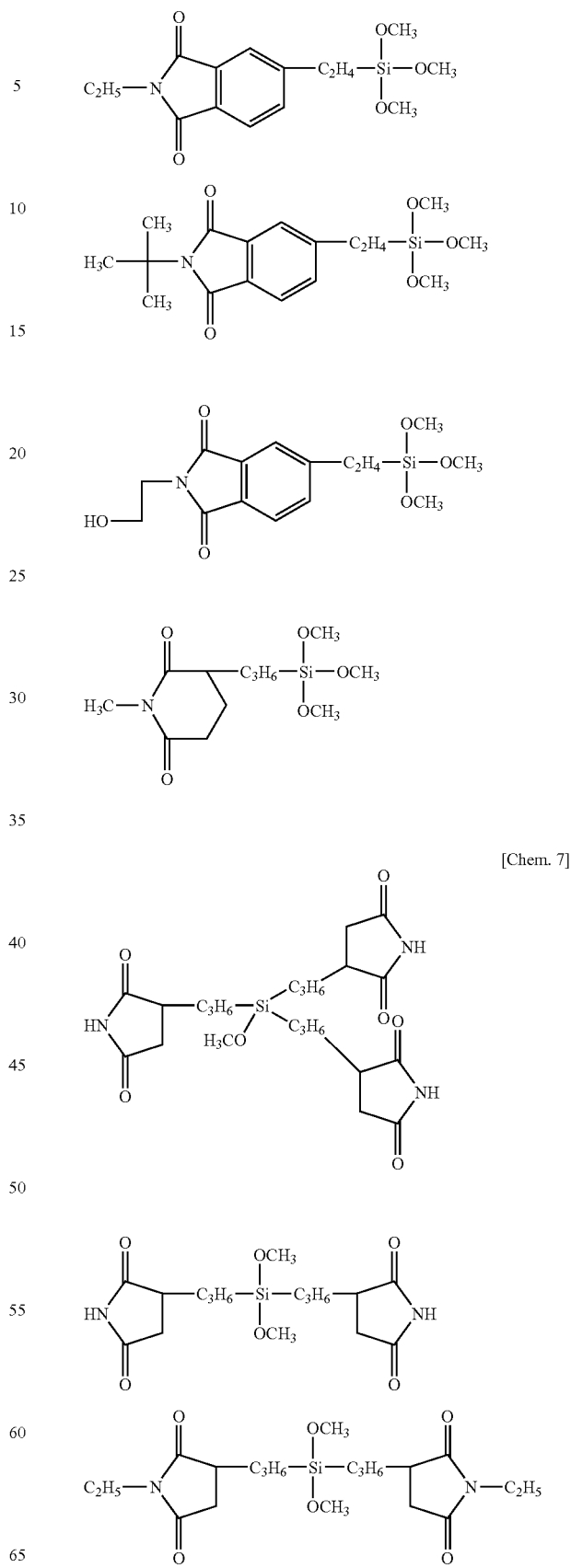

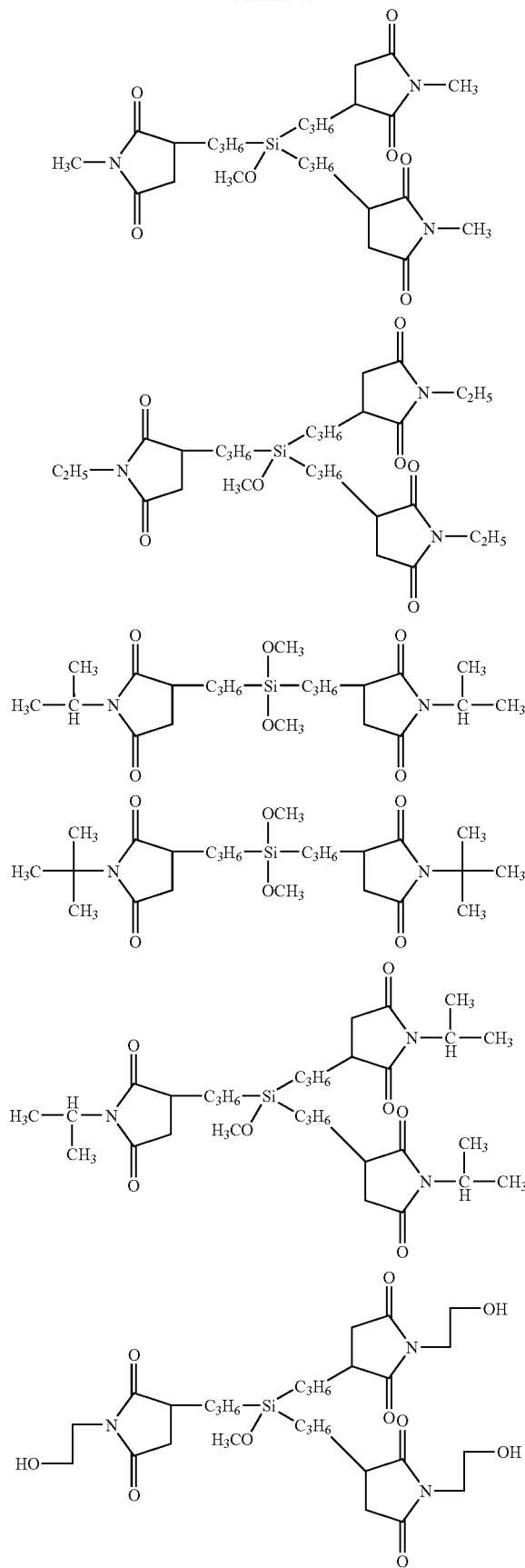
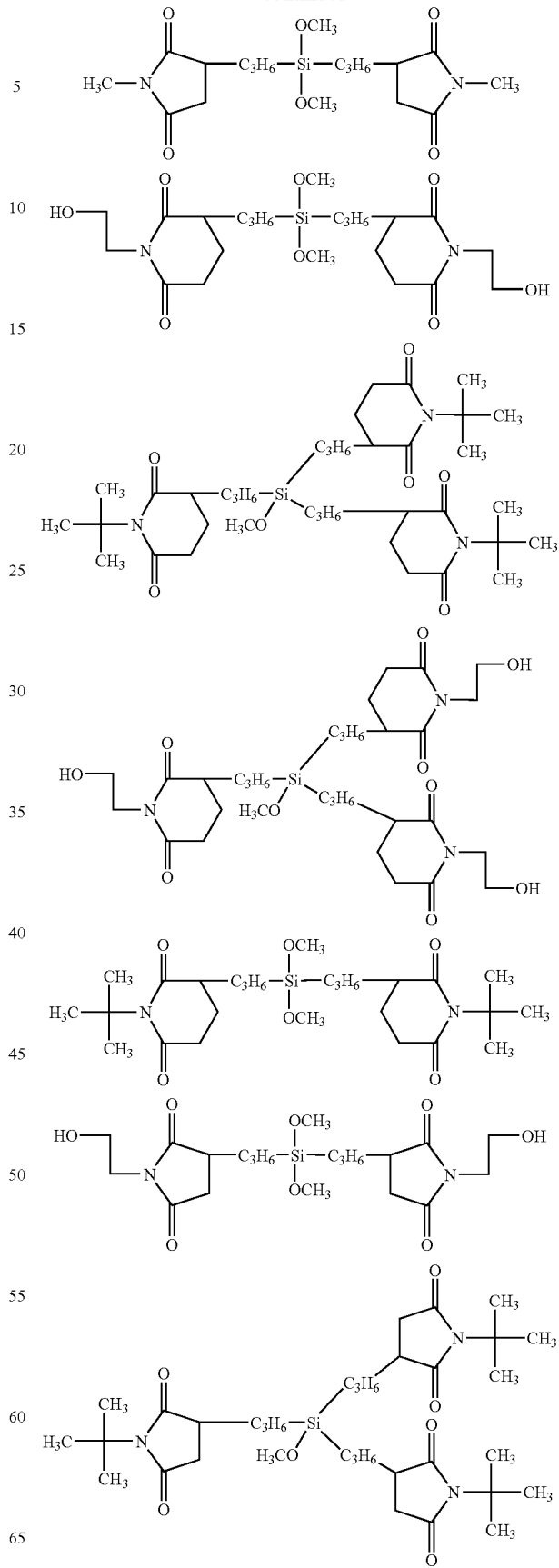

[Chem. 8]

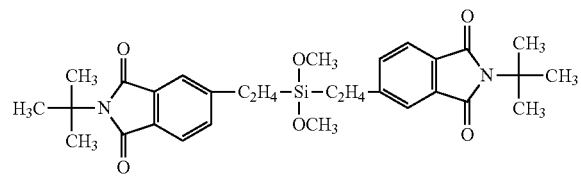

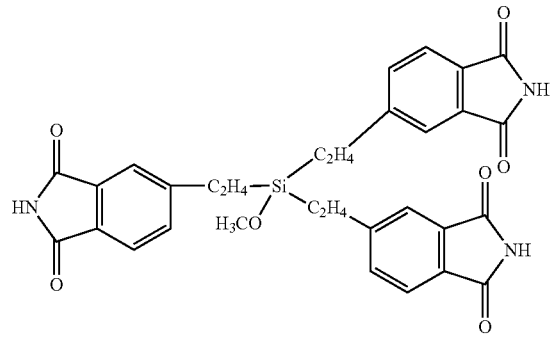

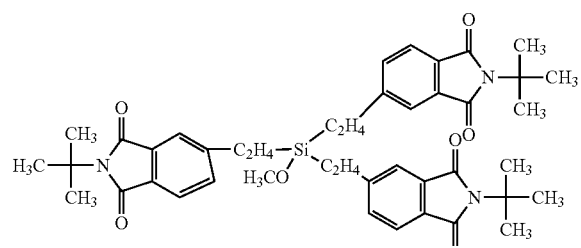

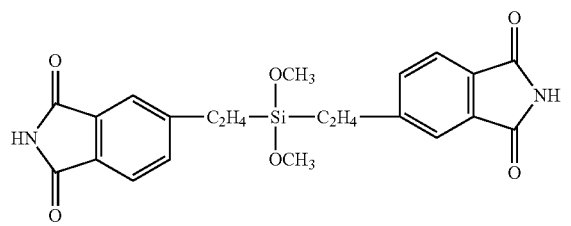

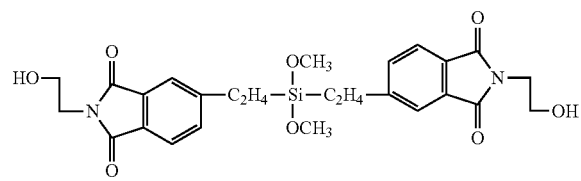

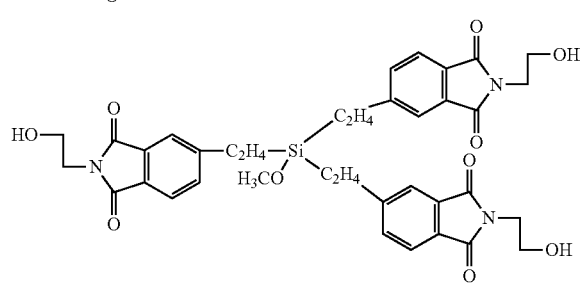

The imidosilane compound represented by formula (4) or (5) can be obtained easily by an imidization method via a known amic acid from a primary amine compound represented by the following formula (9) and an acid anhydride-containing silane compound represented by formula (10) or (11).

[Chem. 9]

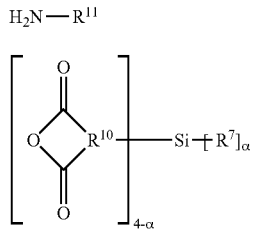

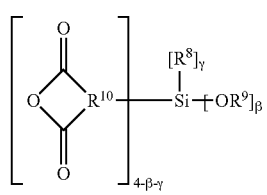

In formula (9), $R^{11}$ represents a hydrogen atom or a silicon atom-free monovalent organic group having 1 to 20 carbon atoms.

In formulas (10) and (11), $R^7$, which may be the same or different, represents an alkyl group having 1 to 6 carbon atoms, an alkoxyl group having 1 to 6 carbon atoms, a phenyl group, a phenoxy group, or a substituted analogue thereof. $R^8$ and $R^9$, which each may be the same or different, each represent a hydrogen atom, an alkyl group having 1 to 6 carbon atoms, a phenyl group, or a substituted analogue thereof. $R^{18}$, which may be the same or different, represents a trivalent organic group having 3 to 30 carbon atoms. $\alpha$ represents an integer of 1 to 3. $\beta$ represents an integer of 1 to 3, and $\gamma$ represents an integer of 0 to 2, provided that $\beta+\gamma<4$.

In the first embodiment of the siloxane-based resin composition of the present invention, the content of the imidosilane compound represented by formula (4) (b) is preferably 0.1 parts by weight or more relative to 100 parts by weight of the siloxane-based resin (a); if so, it is possible to enhance the adhesion, the crack resistance, and the solvent resistance of a cured filmmore. Moreover, it is more preferably 4 parts by weight or more; if so, it is possible to reduce the cure shrinkage ratio and enhance the crack resistance more. On the other hand, it is preferably 20 parts by weight or less; if so, it is possible to keep the transparency of a cured film high.

In the second embodiment of the siloxane-based resin composition of the present invention, when the imidosilane compound represented by formula (4) (b) is contained, its content is preferably 0.1 parts by weight or more relative to 100 parts by weight of the siloxane-based resin (a); if so, it is possible to enhance the adhesion, the crack resistance, and the solvent resistance of a cured film more. On the other hand, it is preferably 10 parts by weight or less; if so, it is possible to keep the transparency of a cured film high. The total amount of the residual group of the imidosilane compound represented by formula (5) and the imidosilane compound represented by formula (4) (b) is preferably 1.1 parts by weight or more relative to 100 parts by weight of the siloxane-based resin (a); if so, it is possible to enhance the adhesion, the crack resistance and the solvent resistance more. Moreover, it is more preferably 5 parts by weight or more; if so, it is possible to reduce the cure shrinkage ratio and enhance the crack resistance more. On the other hand, it is preferably 50 parts by weight or less; if so, it is possible to keep the transparency of a cured film high.

The siloxane-based resin composition of the present invention preferably contains an acid generator or base generator (c). If so, curing is promoted and it becomes possible to form a cured film within a temperature range of 120° C. to 200° C. Since curing is completed at a low temperature, the molecular motion in a subsequent high temperature heat treatment is small, resulting in small cure shrinkage. Thus, heat stress is reduced and the anticracking is enhanced more.

The acid generator includes a compound that generates an acid with light (henceforth, called a photoacid generator) and a compound that generates an acid with heat (henceforth, called a thermal acid generator). Moreover, the base generator includes a compound that generates a base with light (henceforth, called a photobase generator) and a compound that generates a base with heat (henceforth, called a thermal base generator).

Examples of the photoacid generator include onium salt compounds, halogen-containing compounds, diazoketone compounds, diazomethane compounds, sulfone compounds, sulfonic acid ester compounds, and sulfonimide compounds. Two or more of these may be used together.

Specific examples of the onium salt compound include a diazonium salt, an ammonium salt, an iodonium salt, a sulfonium salt, a phosphonium salt, and an oxonium salt. Examples are diphenyliodonium triflate, diphenyliodonium pyrenesulfonate, diphenyliodonium dodecylbenzenesulfonate, triphenylsulfonium triflate (commercial name "TPS-105", produced by Midori Kagaku Co., Ltd.), 4-t-butylphenyldiphenylsulfonium triflate (commercial name "WPAG-339", produced by Wako Pure Chemical Industries, Ltd.), 4-methoxyphenyldiphenylsulfonium triflate (commercial name "WPAG-370", produced by Wako Pure Chemical Industries, Ltd.), triphenylsulfonium nonaflate (commercial name "TPS-109", produced by Midori Kagaku Co., Ltd.), triphenylsulfonium hexafluoroantimonate, triphenylsulfonium naphthalenesulfonate, and (hydroxyphenyl)benzylmethylsulfonium toluenesulfonate.

Examples of the halogen-containing compound include 1,1-bis(4-chlorophenyl)-2,2,2-trichloroethane, 2-phenyl-4,6-bis(trichloromethyl)-s-triazine, and 2-naphthyl-4,6-bis(trichloromethyl)-s-triazine.

Examples of the diazoketone compound include an ester of 1,2-naphthoquinonediazido-4-sulfonic acid and 2,2,3,4,4'-tetrahydroxybenzophenone, and an ester of 1,2-naphthoquinonediazido-4-sulfonic acid and 1,1,1-tris(4-hydroxyphenyl)ethane.

Examples of the diazomethane compound include diazomethane, methylsulfonyl-p-tosyldiazomethane, cyclohexylsulfonyl(1,1-dimethylethylsulfonyl)diazomethane, bis(1,1-dimethylethylsulfonyl)diazomethane, and phenylslufonyl(benzoyl)diazomethane.

Examples of the sulfone compound include benzoin tosylate, pyrogallol mesylate, and nitrobenzyl-9,10-diethoxyanthracene-2-sulfoate.

Other examples include 5-norbornene-2,3-dicarboxylmidyl triflate (commercial name "NDI-105", produced by Midori Kagaku Co., Ltd.), 5-norbornene-2,3-dicarboxylmidyl naphthalimidyl butanesulfonate, 5-norbornene-2,3-dicarboximidyl tosylate (commercial name "NDI-101", produced by Midori Kagaku Co., Ltd.), 4-methylphenylsulfonyloxyimino-α-(4-methoxyphenyl)acetonitrile (commercial name "PAI-101", produced by Midori Kagaku Co., Ltd.), trifluoromethylsulfonyloxyimino-α-(4-methoxyphenyl)acetonitrile (commercial name "PAI-105", produced by Midori Kagaku Co., Ltd.), 9-camphorsulfonyloxyimino α-4-methoxyphenylacetonitrile (commercial name "PAI-106", produced by Midori Kagaku Co., Ltd.), 1,8-naphthalimidyl butanesulfonate (commercial name "NAI-1004", produced by Midori Kagaku Co., Ltd.), 1,8-naphthalimidyl tosylate (commercial name "NAI-101", produced by Midori Kagaku Co., Ltd.), 1,8-naphthalimidyl triflate (commercial name "NAI-105", produced by Midori Kagaku Co., Ltd.), and 1,8-naphthalimidyl nonafluorobutanesulfonate (commercial name "NAI-109", produced by Midori Kagaku Co., Ltd.).

Usually, the content of the photoacid generator is 1 to 10 parts by weight, and preferably 1 to 7 parts by weight relative to 100 parts by weight of the siloxane-based resin (a). If it is 1 part by weight or more, a curing acceleration effect is obtained sufficiently also when a cured film is formed within a temperature range of 120° C. to 200° C., and the crack resistance and the solvent resistance are enhanced more. If it is 10 parts by weight or less, it is possible to keep the transparency of a cured film high.

Furthermore, such a photoacid generator is preferably used in combination with a 9,10-bisubstituted anthracene-based compound as a sensitizer. Because the 9,10-bisubstituted anthracene-based compound does not produce coloring through a photo-bleaching reaction, a high transparency can be maintained also when it remains in a cured film.

Examples of the 9,10-bisubstituted anthracene-based compound include 9,10-diphenylanthracene, 9,10-bis(4-methoxyphenyl)anthracene, 9,10-bis(triphenylsilyl) anthracene, 9,10-dimethoxyanthracene, 9,10-diethoxyanthracene, 9,10-dipropoxyanthracene, 9,10-dibutoxyanthracene, 9,10-dipentaoxyanthracene, 2-t-butyl-9,10-dibutoxyanthracene, and 9,10-bis(trimethylsilylethynyl)anthracene. Among these, 9,10-dimethoxyanthracene, 9,10-diethoxyanthracene, 9,10-dipropoxyanthracene, and 9,10-dibutoxyanthracene are particularly preferable. As to these sensitizers, two or more agents may be used together.

The content of the sensitizer is usually 0.05 to 5 parts by weight, and preferably 0.1 to 3 parts by weight relative to 100 parts by weight of the siloxane-based resin (a). If it is 0.05 parts by weight or more, the acid generating efficiency by light increases, so that a curing acceleration effect is obtained sufficiently also when a cured film is formed within a temperature range of 120° C. to 200° C., and the crack resistance and the solvent resistance are enhanced more. On the other hand, if it is 5 parts by weight or less, it is possible to keep the transparency of a cured film high.

Specific examples of a thermal acid generator include SI-60, SI-80, SI-100, SI-110, SI-145, SI-150, SI-60L, SI-80L, SI-100L, SI-110L, SI-145L, SI-150L, SI-160L, SI-180L (all are produced by SANSHIN CHEMICAL INDUSTRY CO., LTD.), 4-hydroxyphenyldimethyl sulfonium, benzyl-4-hydroxyphenylmethyl sulfonium, 2-methylbenzyl-4-hydroxyphenyl methyl sulfonium, 2-methylbenzyl-4-acetylphenylmethyl sulfonium, 2-methylbenzyl-4-benzoyloxyphenylmethyl sulfonium, and their methanesulfonic acid salts, trifluoromethane sulfonic acid salts, camphorsulfonic acid salts, and p-toluenesulfonic acid salts. More preferable examples are 4-hydroxyphenyl dimethyl sulfonium, benzyl-4-hydroxyphenyl methyl sulfonium, 2-methylbenzyl-4-hydroxyphenyl methyl sulfonium, 2-methylbenzyl-4-acetylphenylmethyl sulfonium, 2-methylbenzyl-4-benzoyloxyphenylmethylsulfonium, and their trifluoromethane sulfonic acid salts, camphorsulfonic acid salts, and p-toluenesulfonic acid salts. As to these compounds, two or more of them may be used in combination.

Usually, the content of the thermal acid generator is 0.01 to 10 parts by weight, and preferably 0.01 to 5 parts by weight relative to 100 parts by weight of the siloxane-based resin (a). If it is 0.01 part by weight or more, curing proceeds sufficiently also when a cured film is formed within a temperature range of 120° C. to 200° C., and the crack resistance and the solvent resistance are enhanced more. If it is 10 parts by weight or less, it is possible to keep the transparency of a cured film high.

Preferable examples of a photobase generator include propionylacetophenone oxime, propionylbenzophenone oxime, propionylacetone oxime, butyrylacetophenone oxime, butyrylbenzophenone oxime, butyrylacetone oxime, adipoylacetophenone oxime, adipoylbenzophenone oxime, adipoylacetone oxime, acroylacetophenone oxime, acroylbenzophenone oxime, acroylacetone oxime, [[(2-nitrobenzyl)oxy]carbonyl]cyclohexylamine, bis[[(2-nitrobenzyl)oxy]carbonyl]hexamethylenediamine, and bis[[($\alpha,\alpha$-dimethyl-3,5-dimethoxybenzyl)oxy]carbonyl]hexamethylenediamine. Two or more of these may be used together.

Usually, the content of the photobase generator is 1 to 10 parts by weight, and preferably 1 to 7 parts by weight relative to 100 parts by weight of the siloxane-based resin (a). If it is 1 part by weight or more, a curing acceleration effect is obtained sufficiently also when a cured film is formed within a temperature range of 120° C. to 200° C., and the crack resistance and the solvent resistance are enhanced more. If it is 10 parts by weight or less, it is possible to keep the transparency of a cured film high.

Moreover, it is preferable to use, as a sensitizer, one having been provided as an example of the sensitizer for the photoacid generator in combination. The content of the sensitizer is usually 0.05 to 5 parts by weight, and preferably 0.1 to 3 parts by weight relative to 100 parts by weight of the siloxane-based resin (a). If it is 0.05 parts by weight or more, a curing acceleration effect is obtained sufficiently also when a cured film is formed within a temperature range of 120° C. to 200° C., and the crack resistance and the solvent resistance are enhanced more. On the other hand, if it is 5 parts by weight or less, it is possible to keep the transparency of a cured film high.

Specific examples of a thermal base generator include carbamate derivatives, such as 1-methyl-1-(4-biphenylyl)ethylcarbamate and 1,1-dimethyl-2-cyanoethylcarbamate, urea and urea derivatives, such as N,N-dimethyl-N'-methylurea, dihydropyridine derivatives, such as 1,4-dihydronicotinamide, quaternary ammonium salts of organic silanes or organic boranes, and dicyandiamide. Two or more of these may be used together. Among these, 1-methyl-1-(4-biphenylyl)ethylcarbamate, 1,1-dimethyl-2-cyanoethylcarbamate, N,N-dimethyl-N'-methylurea, and 1,4-dihydronicotinamide are preferable.

Usually, the content of the thermal base generator is 0.01 to 10 parts by weight, and preferably 0.01 to 5 parts by weight relative to 100 parts by weight of the siloxane-based resin (a). If it is 0.01 parts by weight or more, a curing acceleration effect is obtained sufficiently also when a cured film is formed within a temperature range of 120° C. to 200° C., and the crack resistance and the solvent resistance are enhanced more. If it is 10 parts by weight or less, it is possible to keep the transparency of a cured film high.

The siloxane-based resin composition of the present invention may contain a solvent so that solid components may be contained at an adequate concentration. Specific examples include ethers, such as ethylene glycol monomethyl ether, ethylene glycol monoethyl ether, propylene glycol monomethyl ether, propylene glycol monoethyl ether, propylene glycol monopropyl ether, propylene glycol monobutyl ether, propylene glycol mono-t-butyl ether, ethylene glycol dimethyl ether, ethylene glycol diethyl ether, and diethylene glycol dibutyl ether; acetates, such as ethylene glycol monoethyl ether acetate, propylene glycol monomethyl ether acetate, propyl acetate, butyl acetate, isobutyl acetate, 3-methoxybutyl acetate, 3-methyl-3-methoxybutyl acetate, methyl lactate, ethyl lactate, and butyl lactate; ketones, such as acetylacetone, methyl propyl ketone, methyl butyl ketone, methyl isobutyl ketone, cyclopentanone, and 2-heptanone; alcohols, such as methanol, ethanol, propanol, butanol, isobutyl alcohol, pentanol, 4-methyl-2-pentanol, 3-methyl-2-butanol, 3-methyl-3-methoxy-1-butanol, and diacetone alcohol; aromatic hydrocarbons, such as toluene and xylene; γ-butyrolactone, and N-methylpyrrolidinone. It is permitted to use two or more of these together. Among these, propylene glycol monomethyl ether, propylene glycol monomethyl ether acetate, propylene glycol monoethyl ether, propylene glycol monopropyl ether, propylene glycol monobutyl ether, propylene glycol mono-t-butyl ether, diacetone alcohol, and γ-butyrolactone are preferable.

The content of the whole solvent in the siloxane-based resin composition of the present invention is preferably 100 to 9900 parts by weight, and more preferably 100 to 5000 parts by weight, relative to 100 parts by weight of the siloxane-based resin (a).

For improving the flowability at the time of application and the uniformity of a film thickness, the siloxane-based resin composition of the present invention may contain various types of surfactant. There is no particular restriction with respect to the type of the surfactant, and a fluorine-based surfactant, a silicone-based surfactant, a polyalkylene oxide-based surfactant, and a poly(meth) acrylate-based surfactant can be used, for example. Two or more of these may be contained. From the viewpoint of flowability and film thickness uniformity, a fluorine-based surfactant is preferable.

As the fluorine-based surfactant, "MEGAFAC (registered trademark)" F172 (commercial name, produced by Dainippon Ink & Chemicals, Inc.), BM-1000 and BM-1100 (commercial names, available from Yusho Co., Ltd.), and NBX-15 and FTX-218 (commercial names, produced by NEOS Co., Ltd.) are particularly preferable from the viewpoint of flowability and film thickness uniformity.

Examples of commercially available silicone-based surfactants include SH28PA, SH7PA, SH21PA, SH30PA, and ST94PA (all produced by Dow Corning Toray Co., Ltd.), and BYK-333 (produced by BYK Japan KK). Examples of other surfactants include polyoxyethylene lauryl ether, polyoxyethylene stearyl ether, polyoxyethylene nonyl phenyl ether, and polyoxyethylene distearate.

The content of the surfactant is usually 0.001 to 10 parts by weight relative to 100 parts by weight of the siloxane-based resin (a).

The siloxane-based resin composition of the present invention may, as necessary, contain a viscosity modifier, a stabilizer, a colorant, a glassy substance forming agent, and so on.

Moreover, the siloxane-based resin composition of the present invention may contain (d) a crosslinking compound that has a group represented by the following formula (6) or (7) and has no silicon atom and/or a crosslinking compound represented by the following formula (8), which promotes the curing of the siloxane-based resin composition or makes the curing easier. Because of the inclusion of such a crosslinking compound, the siloxane-based resin (a), which is a matrix material, bonds firmly when the siloxane-based resin composition of the present invention is cured, so that a high heat cycling property is obtained and a cured film excellent in anticracking can be formed. Two or more of these may be contained.

[Chem. 10]

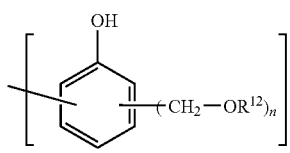
(6)

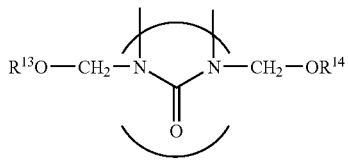
(7)

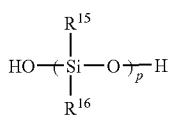
(8)

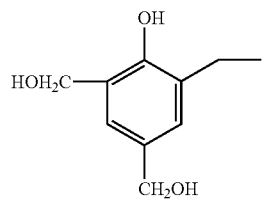
46DMOEP

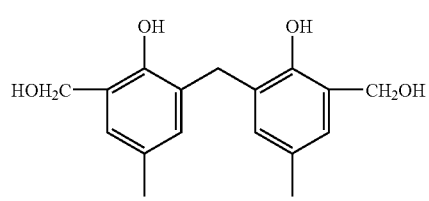
DML-MBPC

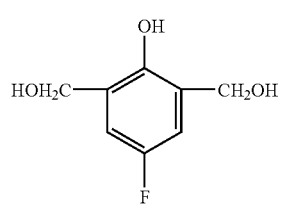
DML-PFP

In formula (6), $R^{12}$, which may be the same or different, represents a hydrogen atom or a monovalent organic group. n represents an integer of 1 to 4. In formula (7), $R^{13}$ and $R^{14}$ each represent a hydrogen atom or a monovalent organic group. Specific examples of $R^{12}$ to $R^{14}$ include a hydrogen atom, alkyl groups, such as a methyl group, an ethyl group, a propyl group, and a butyl group, and aryl groups, such as a phenyl group. From the viewpoint of the temporal stability of a resin composition and the reactivity of a crosslinking compound, a methyl group and an ethyl group are preferred. In formula (8), $R^{15}$ and $R^{16}$, which each may be the same or different, each represent an alkyl group having 1 to 4 carbon atoms, a phenyl group, or a substituted analogue thereof, provided that at least one of p $R^{15}$ and $R^{16}$ are a phenyl group or its substituted analogue. Examples of the substituents of the substituted analogue of the alkyl group or the phenyl group include a $CF_3$ group, a $CH_2CF_3$ group, a $C_2H_4CF_3$ group, a $C_6H_4$—$CH_3$ group, and a $C_6H_4$t-Bu group. From the viewpoint of increasing the refractive index and increasing the crack resistance more, $R^{15}$ and $R^{16}$ are preferably methyl groups or phenyl groups. p represents an integer of 4 to 20.

The following are specific examples of the crosslinking compound which has a group represented by formula (6) and has no silicon atom.

[Chem. 11]

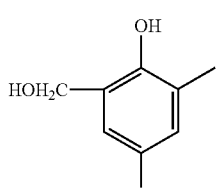
46DMOC

DML-PSBP

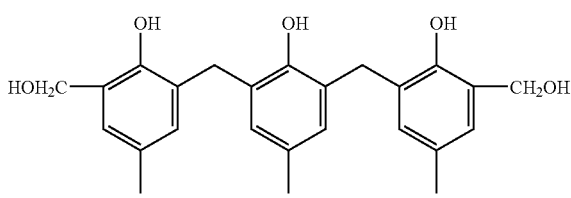
DML-MTrisPC

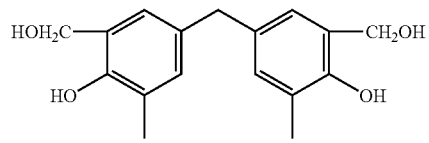
DML-MBOC

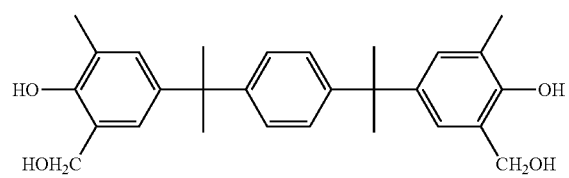
dimethylol-BisOC-P

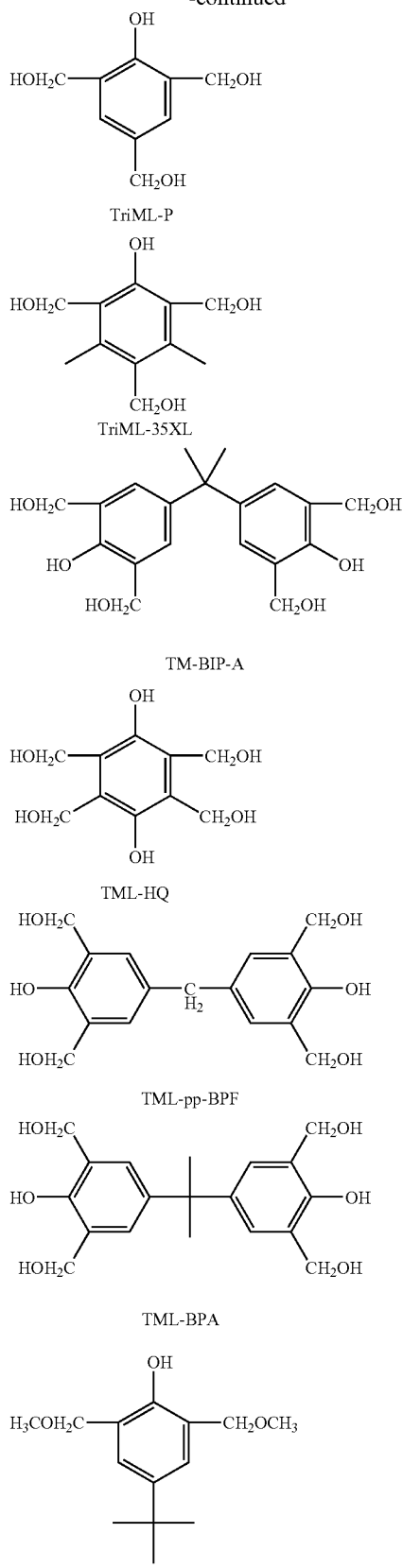
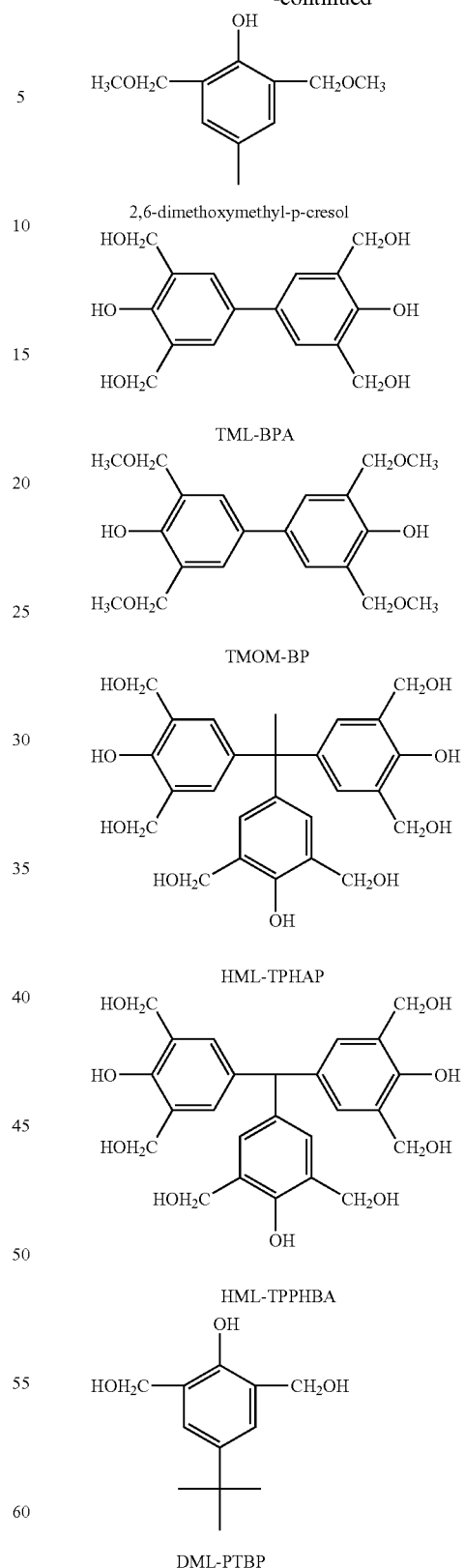
The following are specific examples of the crosslinking compound which has a group represented by formula (7) and has no silicon atom.
[Chem. 12]

[Chem. 13]

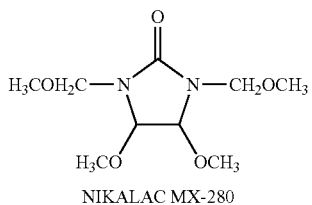
NIKALAC MX-280

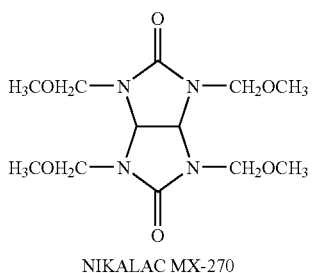
NIKALAC MX-270

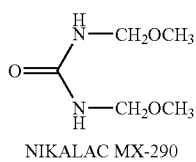
NIKALAC MX-290

Even inside of the above, 2,2-dimethoxymethyl-4-t-butyl phenol, 2,2-dimethoxymethyl-p-cresol, TML-BPA, TMOM-BP, and HML-TPHAP, which have a group represented by formula (6), and "NIKALAC (registered trademark)" MX-280 and "NIKALAC" MX-270 (commercial names, produced by SANWA CHEMICAL CO., LTD.), which have a group represented by formula (7) are preferable from the viewpoint of crack resistance. Furthermore, when forming a cured film at a high temperature of 280° C. or higher, compounds containing no phenolic hydroxyl group are preferred and "NIKALAC" MX-280 and "NIKALAC" MX-270 are preferable from the viewpoint of the transparency of a cured film.

Specific examples of the crosslinking compound represented by formula (8) are provided below. Since such a crosslinking compounds has a phenyl group, it can increase the transmittance of a resulting composition more while keeping the refractive index of the composition high. Moreover, the inclusion of such a crosslinking compound makes it possible to more enhance the crack resistance because the crosslinking compound undergoes a curing reaction during the heat treatment of the composition unlike the inclusion of a reaction product obtained by making the crosslinking compound undergo a condensation reaction.

[Chem. 14]

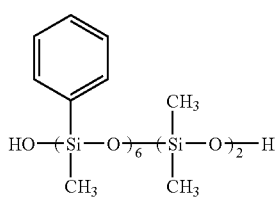
S-1

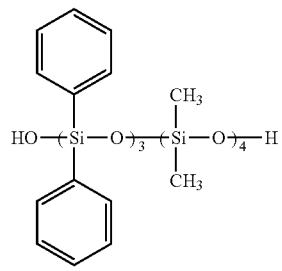
S-2

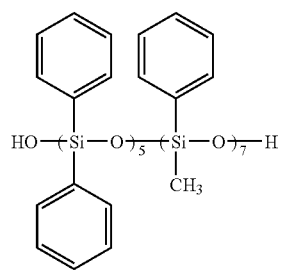
S-3

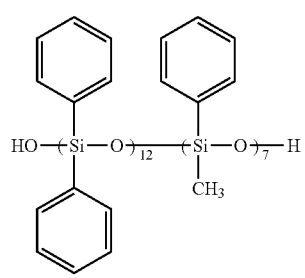
S-4

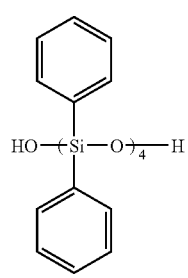
S-11

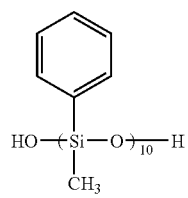
S-12

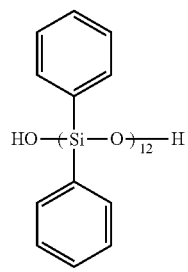
S-13

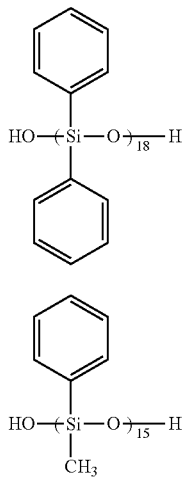

S-14

S-15

Among the crosslinking compounds represented by formula (8), it is preferable that the molar ratio of the alkyl groups to the phenyl groups in $R^{15}$ and $R^{16}$ (i.e., alkyl groups/phenyl groups) be 0 to 1 because if so, it is possible to enhance the transmittance and the crack resistance more. Specifically, S-3, S-4, S-11, S-12, S-13, S-14, and S-15 are preferable.

The crosslinking compound having a group represented by formula (6) or (7) is an organic compound which no silicon atom, and even if its content is small, the effect of enhancing the crack resistance is shown remarkably. In the present invention, the content of such a crosslinking compound is preferably 0.1 parts by weight or more, and more preferably 0.5 parts by weight or more relative to 100 parts by weight of the siloxane-based resin (a) in the siloxane-based resin composition. On the other hand, it is preferably 20 parts by weight or less, and more preferably 10 parts by weight or less. If the content is within such a range, it is possible to inhibit oxidation deterioration of the crosslinking compound caused by heat treatment and maintain the transmittance and the refractive index at a higher level. For making a cure shrinkage ratio small, the content is preferably 3 parts by weight or more.

On the other hand, the crosslinking compound represented by formula (8) is a compound having a silicon atom and it is preferably contained more than the crosslinking compound represented by formula (6) or (7) Specifically, the content is preferably 10 parts by weight or more, and more preferably 20 parts by weight or more relative to 100 parts by weight of the siloxane-based resin (a) in the siloxane-based resin composition. Inclusion in an amount of 10 parts by weight makes it possible to enhance the crack resistance more. For making the cure shrinkage ratio small, the content is 30 parts by weight or more. On the other hand, it is preferably 50 parts by weight or less, and more preferably 40 parts by weight or less.

When using the aforementioned crosslinking compound together, their overall content is preferably 10 parts by weight or more, and more preferably 20 parts by weight or more relative to 100 parts by weight of the siloxane-based resin (a) in the siloxane-based resin composition. On the other hand, it is more preferably 40 parts by weight or less. In this case, the content of the crosslinking compound represented by formula (6) or (7) is preferably 0.1% by weight or more, and more preferably 0.5% by weight or more relative to the overall amount of the solids in the siloxane-based resin composition. On the other hand, it is preferably 20% by weight or less, and more preferably 10% by weight or less.

In the present invention, when the crosslinking compound is contained together with the acid generator or base generator (c), it is possible to enhance the crack resistance remarkably due to their synergistic effect.

Next, the method for producing the siloxane-based resin composition of the present invention is described. The siloxane-based resin composition of the present invention can be obtained by mixing the siloxane-based resin (a) and, in the first embodiment, the imidosilane compound (b) and, as necessary, the acid generator or base generator (c), a crosslinking compound, a surfactant, and so on. At this time, dilution with an arbitrary solvent may be done. The mixing temperature, which is not particularly limited, is preferably within the range of 5 to 50° C. from the viewpoint of the simplicity of operations.

The siloxane-based resin composition of the present invention is suitably used as a material for image sensors. For example, when the refractive index is 1.60 to 1.80, it is used suitably as an embedding planarization film material for waveguides; whereas when the refractive index is less than 1.6, it is used suitably as a planarization film material of a color filter.

A cured film can be formed by applying the siloxane-based resin composition of the present invention onto a base material to obtain an applied film and then curing it. Heating is common as a method for curing the applied film and, as necessary, the applied film may be dried by heating.

As a method for applying a siloxane-based resin composition in the present invention, microgravure coating, spin coating, dip coating, curtain flow coating, roll coating, spray coating, flow coating method, and so on can be used preferably.

The conditions of heating and drying are chosen depending upon a base material and a resin composition to be applied, it is generally preferable to perform treatment for 0.5 minutes to 240 minutes at a temperature of from room temperature to 400° C. A particularly preferable curing temperature is 100 to 400° C., and more preferably 150 to 400° C.

The thickness of the applied film and the thickness of the film after curing, which are not particularly limited, are commonly within the range of 0.001 to 100 mm.

An applied film and a cured film formed from the siloxane-based resin composition of the present invention are used suitably for optical objects, such as an image sensor and an optical filter for a display, such as a liquid crystal display. In more detail, they can be used for a planarization film of an image sensor or an embedding planarization film for waveguides. Moreover, they can be used for low refractive index layers, high refractive index layers, and hard coat layers of antireflection films or antireflection boards of optical filters.

EXAMPLES

The present invention will be described below with reference to examples and technologies, but the invention is not limited by these examples. The evaluations of the resin compositions in examples was carried out by the following methods.

(1) Preparation of a Cured Film

An applied film with a thickness of 2 μm was obtained by applying a siloxane-based resin composition to a 6-inch silicon wafer or a glass substrate with sides 40 mm long by using a spin coater (1H-360S produced by MIKASA CO., LTD.) at an arbitrary rotation rate, and then prebaking it for 3 minutes at 120° C. under an air atmosphere by using a hot plate (SCW-636, manufactured by Dainippon Screen Mfg. Co., Ltd.).

In the case of the resin composition containing a photoacid generator or a photobase generator, a resulting applied film was subjected to full exposure to UV rays (bleaching exposure, primary wavelengths: 365 nm, 405 nm, and 436 nm) for three minutes at a UV intensity of about 5 mW/cm$^2$ (converted to a wavelength of 365 nm) by using an aligner (Contact aligner PLA501, manufactured by Canon Inc.). Subsequently, it was heated at 250° C. for 5 minutes and then at 300° C. for 5 minutes on a hot plate under an air atmosphere, so that a cured film was obtained.

In the case of a resin composition containing neither a photoacid generator nor a photobase generator, an obtained applied film was heated at 250° C. for 5 minutes and then at 300° C. for 5 minutes on a hot plate under an air atmosphere, so that a cured film was obtained.

(2) Measurement of a Refractive Index and a Film Thickness

For a cured film formed on a 6-inch silicon wafer by the method described in (1) above, a film thickness and a refractive index (TE) in a direction perpendicular to a film surface at 23° C. at 633 nm (using a He—Ne laser) by using a prism coupler MODEL 2010 (manufactured by Metricon Corporation).

(3) Measurement of Transmittance

For a cured film formed on a glass substrate with sides 40 mm long by the method described in (1) above, a transmittance at 400 nm was measured by using a UV-VIS spectrophotometer UV-260 (manufactured by SHIMADZU CORPORATION) and then a transmittance was calculated for a film thickness of 1.0 μm.

(4) Evaluation of Crack Resistance

For a cured film formed on a 6-inch silicon wafer by the method described in (1) above, a heat cycle test was carried out in the following temperature history, and the existence of cracks was observed at each temperature with an optical microscope. Heating was performed on a hot plate under an air atmosphere. The temperature history of a heat cycle test: 250° C., 5 minutes->room temperature (23° C.), 5 minutes->280° C., 5 minutes->room temperature (23° C.), 5 minutes->300° C., 5 minutes->room temperature (23° C.), 5 minutes->320° C., 5 minutes->room temperature (23° C.), 5 minutes->340° C., 5 minutes->room temperature (23° C.), 5 minutes->360° C., 5 minutes->room temperature (23° C.), 5 minutes->380° C., 5 minutes->room temperature (23° C.), 5 minutes->400° C., 5 minutes->room temperature (23° C.), 5 minutes->420° C., 5 minutes->room temperature (23° C.), 5 minutes->440° C., 5 minutes->room temperature (23° C.), 5 minutes->460° C., 5 minutes->room temperature (23° C.), 5 minutes.

(5) Evaluation of Adhesion

For the cured film formed on the glass substrate with sides 40 mm long by the method described in the foregoing (1), the adhesion was evaluated in accordance with the crosscut tape method prescribed JIS K5400 8.5.2 (1990). For the cured film, 100 squares (1 mm×1 mm) were formed on the surface of the thin film disposed on the glass substrate with sides 40 mm long by forming eleven parallel straight cuts vertically and eleven parallel straight cuts horizontally at 1 mm intervals by using a cutter, the former eleven cuts perpendicularly intersecting the latter eleven cuts, so that the cuts might reach the glass substrate. A cellophane adhesive tape (width=18 mm, adhesive power=3.7 N/10 mm) was stuck on the surface of the cut thin film and was adhered firmly by being rubbed with an eraser (JIS S6050 acceptable). Then the tape was picked up at its one end and was peeled in a moment while being maintained perpendicular to the substrate. At this time, the number of remaining squares was visually evaluated.

(6) Evaluation of Planarization Performance

For a cured film formed on a silicon wafer by the method described in (1) above, a cure shrinkage ratio of before and after curing was calculated. When this value is 0 to 15%, it can be said that the planarization performance is good. The cure shrinkage ratio was calculated in accordance with the following formula.

Cure shrinkage ratio (%)=(1−Thickness of cured film obtained by cure/thickness of applied film)×100.

Synthesis Example 1

Synthesis of Imidosilane Compound (i)

After 41.97 g (160 mmol) of 3-trimethoxysilylpropylsuccinic anhydride and 11.70 g (160 mmol) of t-butylamine were added to 400 g of propylene glycol monomethyl ether and they were stirred at room temperature for 30 minutes, and stirring was carried out at 60° C. for 2 hours. Then, the temperature was raised to 140° C. and a reaction was performed for 6 hours under azeotropy of propylene glycol monomethyl ether and water. The resulting solution was diluted with diacetone alcohol so that the solid concentration would become 20% by weight and thus a solution of imidosilane compound (i) represented by the following structure was obtained.

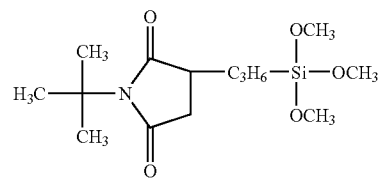

[Chem. 15]

Synthesis Example 2

Synthesis of Imidosilane Compound (ii)

After 23.71 g (80 mmol) of 2-trimethoxysilylethylphthalic anhydride and 4.89 g (80 mmol) of monoethanolamine were added to 400 g of diacetone alcohol and they were stirred at room temperature for 30 minutes, stirring was carried out at 60° C. for 2 hours. Then, the temperature was raised to 140° C. and a reaction was performed for 6 hours under azeotropy of propylene glycol monomethyl ether and water. The resulting solution was diluted with diacetone alcohol so that the solid concentration would become 20% by weight and thus a solution of imidosilane compound (ii) represented by the following structure was obtained.

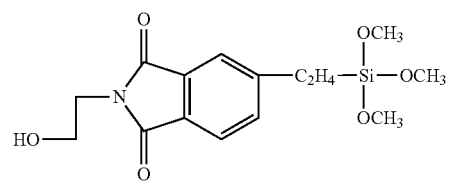

[Chem. 16]

Synthesis Example 3

Synthesis of Imidosilane Compound (iii)

After 20.99 g (80 mmol) of 3-trimethoxysilylpropylsuccinic anhydride and 7.45 g (80 mmol) of aniline were added to 400 g of propylene glycol monomethyl ether acetate and they were stirred at room temperature for 30 minutes, stirring was carried out at 60° C. for 2 hours. Then, the temperature was raised to 160° C. and a reaction was performed for 6 hours under azeotropy of propylene glycol monomethyl ether and water. The resulting solution was diluted with diacetone alcohol so that the solid concentration would become 20% by weight and thus a solution of imidosilane compound (iii) represented by the following structure was obtained.

[Chem. 17]

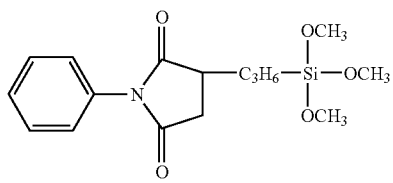

Synthesis Example 4

Synthesis of Imidosilane Compound (iv)

To 40 g of γ-butyrolactone was added 32.84 g (160 mmol) of isocyanate propyltrimethoxysilane, which was then dissolved under stirring. After 23.70 g (160 mmol) of phthalic anhydride was added and stirred at room temperature for 30 minutes, stirring was carried out at 140° C. for 2 hours. The resulting solution was diluted with γ-butyrolactone so that the solid concentration would become 20% by weight and thus a solution of imidosilane compound (iv) represented by the following structure was obtained.

[Chem. 18]

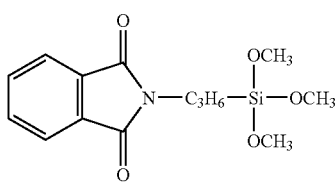

Synthesis Example 5

Synthesis of Imidosilane Compound (v)

After 35.42 g (160 mmol) of aminopropyltriethoxysilane and 16.01 g (160 mmol) of succinic anhydride were added to 400 g of diacetone alcohol and they were stirred at room temperature for 30 minutes, stirring was carried out at 60° C. for 2 hours. Then, the temperature was raised to 160° C. and a reaction was performed for 6 hours under azeotropy of diacetone alcohol and water. The resulting solution was diluted with diacetone alcohol so that the solid concentration would become 20% by weight and thus a solution of imidosilane compound (v) represented by the following structure was obtained.

[Chem. 19]

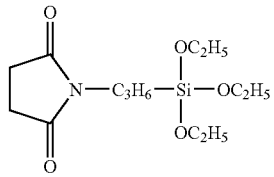

Synthesis Example 6

Synthesis of Aromatic Bisimide Oligomer (vi)

To a vessel equipped with a stirrer, a reflux condenser, and a nitrogen introduction tube were added 32.58 g (220 mmol) of phthalic anhydride, 1.39 g of γ-picoline, and 130.3 g of N-methyl-2-pyrrolidone (henceforth, abbreviated as NMP), and then a solution resulting from dissolution of 24.8 g (100 mmol) of 1,3-bis(3-aminopropyl)tetramethyldisiloxane in 99.4 g of NMP was added dropwise thereto, followed by stirring in a nitrogen atmosphere for 2 hours. Then, 40.8 g (400 mmol) of acetic anhydride was added and the temperature was raised to 70° C. by heating under agitation in a nitrogen atmosphere and a reaction was carried out at 70° C. for 4 hours. After the completion of the reaction, the resultant was cooled to room temperature and poured into 2000 ml of water, so that 43.24 g of bisimide powder was obtained. When the infrared absorption spectrum of this bisimide powder was measured, characteristic absorption of an imide ring was observed at 1720 cm$^{-1}$ and 1780 cm$^{-1}$. The resulting bisimide powder was dissolved in γ-butyrolactone so that the solid concentration would become 20% by weight and thus a solution of an aromatic bisimide oligomer (vi) represented by the following structure was obtained.

[Chem. 20]

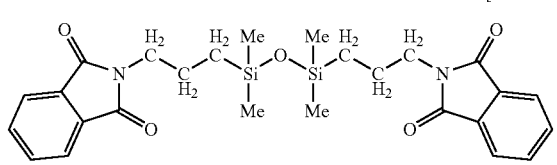

Synthesis Example 7

Synthesis of Silicone Polyimide Precursor (vii)

To 40 g of γ-butyrolactone was added 35.42 g (160 mmol) of aminopropyltriethoxysilane, which was then dissolved under stirring. After 24.82 g (80 mmol) of 4,4'-oxydiphthalic dianhydride was added and stirred at room temperature for 30 minutes, stirring was carried out at 40° C. for 2 hours. The resulting solution was diluted with γ-butyrolactone so that the solid concentration would become 20% by weight and thus a solution of a silicone polyimide precursor (vii) represented by the following structure was obtained.

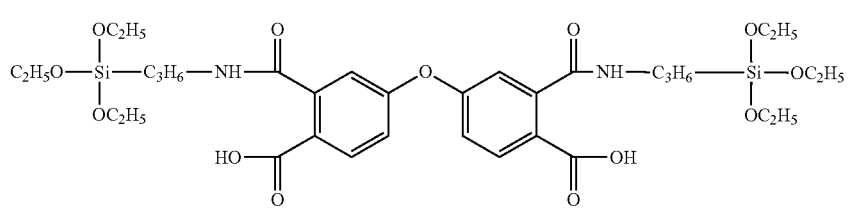

[Chem. 21]

Synthesis Example 8

Synthesis of Imidosilane Compound (viii)

After 29.80 g (80 mmol) of dimethoxysilyl-3,3'-bis(propylsuccinic anhydride) and 11.70 g (160 mmol) of t-butylamine were added to 400 g of propylene glycol monomethyl ether and they were stirred at room temperature for 30 minutes, stirring was carried out at 60° C. for 2 hours. Then, the temperature was raised to 140° C. and a reaction was performed for 6 hours under azeotropy of propylene glycol monomethyl ether and water. The resulting solution was diluted with diacetone alcohol so that the solid concentration would become 20% by weight and thus a solution of imidosilane compound (viii) represented by the following structure was obtained.

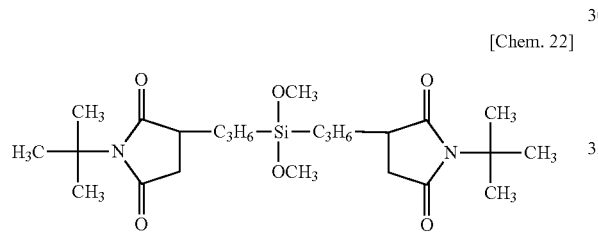

[Chem. 22]

Synthesis Example 9

Synthesis of Imidosilane Compound (ix)

After 35.24 g (80 mmol) of dimethoxysilyl-2,2'-bis(ethylphthalic anhydride) and 9.78 g (160 mmol) of monoethanolamine were added to 400 g of diacetone alcohol and they were stirred at room temperature for 30 minutes, stirring was carried out at 60° C. for 2 hours. Then, the temperature was raised to 140° C. and a reaction was performed for 6 hours under azeotropy of propylene glycol monomethyl ether and water. The resulting solution was diluted with diacetone alcohol so that the solid concentration would become 20% by weight and thus a solution of imidosilane compound (ix) represented by the following structure was obtained.

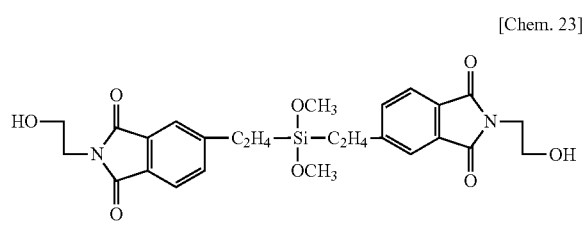

[Chem. 23]

Synthesis Example 10

Synthesis of Imidosilane Compound (x)

After 24.13 g (50 mmol) of methoxysilyl-3,3',3''-tris(propylsuccinic anhydride) and 8.87 g (150 mmol) of i-propylamine were added to 400 g of propylene glycol monomethyl ether and they were stirred at room temperature for 30 minutes, stirring was carried out at 60° C. for 2 hours. Then, the temperature was raised to 140° C. and a reaction was performed for 6 hours under azeotropy of propylene glycol monomethyl ether and water. The resulting solution was diluted with diacetone alcohol so that the solid concentration would become 20% by weight and thus a solution of imidosilane compound (x) represented by the following structure was obtained.

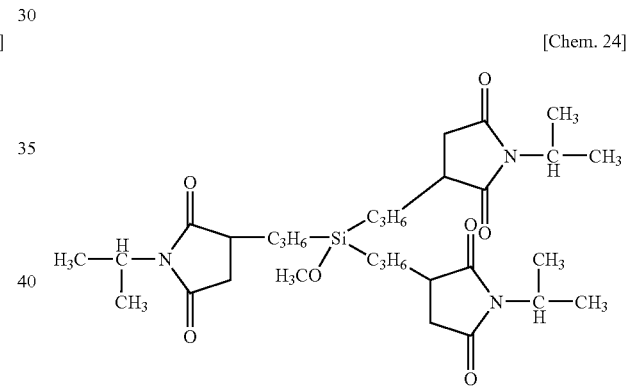

[Chem. 24]

Example 1

Into a reaction vessel were charged 20.4 g (0.15 mol) of methyltrimethoxysilane, 69.4 g (0.35 mol) of phenyltrimethoxysilane, 70.6 g of "Optolake" TR-521 with a number average particle diameter of 15 nm (commercial name, produced by Catalysts & Chemicals Industries Co., Ltd., composition: 30% by weight of titanium oxide particles and 70% by weight of γ-butyrolactone), and 44.1 g of γ-butyrolactone, and to the resulting solution were added dropwise 30.6 g of water and 0.48 g of phosphoric acid under stirring in such a manner that the reaction temperature would not exceed 40° C. After the adding, a distillation apparatus was attached to a flask, and the resulting solution was heated and stirred at a bath temperature of 105° C. for 2.5 hours, thereby being reacted under evaporation of methanol generated by hydrolysis. Then, the solution was further heated and stirred at a bath temperature of 130° C. for 2 hours and then cooled to room temperature, so that a polymer solution A (with a solid concentration of 55% by weight) was obtained. Into 10 g of the resulting polymer solution A were added and dissolved 10 g of γ-butyrolactone and 2.5 g of an imidosilane compound (i) solution (with a solid content of 0.5 g), so that a siloxane-based resin composition 1 was obtained.

Using the resulting siloxane-based resin composition 1, evaluation was performed with respect to a refractive index, a transmittance, crack resistance, adhesion, and planarization performance by the above-described methods.

Example 2

Into a reaction vessel were charged 8.2 g (0.06 mol) of methyltrimethoxysilane, 55.5 g (0.28 mol) of phenyltrimethoxysilane, 7.2 g (0.06 mol) of dimethyldimethoxysilane, 71.1 g of "Optolake" TR-521 with a number average particle diameter of 15 nm, and 23.9 g of γ-butyrolactone, and to the resulting solution were added dropwise 34.5 g of water and 1.0 g of phosphoric acid under stirring in such a manner that the reaction temperature would not exceed 40° C. After the adding, a distillation apparatus was attached to a flask, and the resulting solution was heated and stirred at a bath temperature of 105° C. for 2.5 hours, thereby being reacted under evaporation of methanol generated by hydrolysis. Then, the solution was further heated and stirred at a bath temperature of 130° C. for 2 hours and then cooled to room temperature, so that a polymer solution B (with a solid concentration of 48% by weight) was obtained. Into 10 g of the resulting polymer solution B were added and dissolved 10 g of γ-butyrolactone, 0.24 g of a crosslinking compound "NIKALAC" MX-270 (produced by SANWA Chemical Co., Ltd.), and 3.6 g of an imidosilane compound (II) solution (with a solid content of 0.72 g), so that a siloxane-based resin composition 2 was obtained.

A cured film was prepared by using the resulting siloxane-based resin composition 2, and evaluation was performed with respect to a refractive index, a transmittance, crack resistance, adhesion, and planarization performance by the above-described methods.

Example 3

A siloxane-based resin composition 3 was obtained in the same manner as in Example 2 except for not using NIKALAC MX-270.

A cured film was prepared by using the resulting siloxane-based resin composition 3, and evaluation was performed with respect to a refractive index, a transmittance, crack resistance, adhesion, and planarization performance by the above-described methods.

Example 4

A polymer solution C (solid concentration: 46% by weight) was obtained by carrying out the same operations as those of Example 2 except for using 70.0 g of a propylene glycol monomethyl ether acetate dispersion liquid of zirconium oxide particles with a number average particle diameter of 30 nm (zirconium oxide: 30% by weight, propylene glycol monomethyl ether acetate: 70% by weight) instead of 71.1 g of "Optolake" TR-521. Into 10 g of the resulting polymer solution C were added and dissolved 15 g of propylene glycol monomethyl ether acetate and 2.05 g of an imidosilane compound (i) solution (with a solid content of 0.41 g), so that a siloxane-based resin composition 4 was obtained.

A cured film was prepared by using the resulting siloxane-based resin composition 4, and evaluation was performed with respect to a refractive index, a transmittance, crack resistance, adhesion, and planarization performance by the above-described methods.

Example 5

A polymer solution D (solid concentration: 40% by weight) was obtained by carrying out the same operations as those of Example 2 except for using 45.0 g of a propylene glycol monomethyl ether acetate dispersion liquid of aluminum oxide particles with a number average particle diameter of 30 nm (aluminum oxide: 30% by weight, propylene glycol monomethyl ether acetate: 70% by weight) instead of 71.1 g of "Optolake" TR-521. Into 10 g of the resulting polymer solution D were added and dissolved 20 g of 3-methyl-3-methoxybutyl acetate, 0.12 g of a thermal acid generator, benzyl-4-hydroxyphenyl methyl sulfonium trifluoromethanesulfonate (BHPMT), and 1.8 g of imidosilane compound (i) solution (with a solid content of 0.36 g), so that a siloxane-based resin composition 5 was obtained.

A cured film was prepared by using the resulting siloxane-based resin composition 5, and evaluation was performed with respect to a refractive index, a transmittance, crack resistance, adhesion, and planarization performance by the above-described methods.

Example 6

A siloxane-based resin composition 6 was obtained in the same manner as in Example 5 except for not using BHPMT. A cured film was prepared by using the resulting siloxane-based resin composition 6, and evaluation was performed with respect to a refractive index, a transmittance, crack resistance, adhesion, and planarization performance by the above-described methods.

Example 7

Into a reaction vessel were charged 8.2 g (0.06 mol) of methyltrimethoxysilane, 55.5 g (0.28 mol) of phenyltrimethoxysilane, 5.4 g (0.026 mol) of tetraethoxysilane, 52.4 g of "Optolake" TR-521, and 20.5 g of γ-butyrolactone, and to the resulting solution were added dropwise 34.5 g of water and 1.0 g of phosphoric acid under stirring in such a manner that the reaction temperature would not exceed 40° C. After the adding, a distillation apparatus was attached to a flask, and the resulting solution was heated and stirred at a bath temperature of 105° C. for 2.5 hours, thereby being reacted under evaporation of methanol and ethanol generated by hydrolysis. Then, the solution was further heated and stirred at a bath temperature of 130° C. for 2 hours and then cooled to room temperature, so that a polymer solution E (with a solid concentration of 60% by weight) was obtained. Into 20 g of the resulting polymer solution E were added and dissolved 40 g of γ-butyrolactone, 0.48 g of 5-norbornene-2,3-dicarboximidyl tosylate (commercial name: NDI-101, produced by Midori Kagaku Co., Ltd.), which is a photoacid generator, 0.036 g of 9,10-dibutoxyanthracene (DBA), which is a sensitizer, and 0.12 g of an imidosilane compound (II) solution (with a solid content of 0.024 g), so that a siloxane-based resin composition 7 was obtained.

A cured film was prepared by using the resulting siloxane-based resin composition 7, and evaluation was performed with respect to a refractive index, a transmittance, crack resistance, adhesion, and planarization performance by the above-described methods.

Example 8

A siloxane-based resin composition 8 was obtained in the same manner as in Example 7 except for not using NDI-101 and DBA. A cured film was prepared by using the resulting siloxane-based resin composition 8, and evaluation was performed with respect to a refractive index, a transmittance, crack resistance, adhesion, and planarization performance by the above-described methods.

Example 9

Into a reaction vessel were charged 12.3 g (0.15 mol) of methyltrimethoxysilane, 41.6 g (0.35 mol) of phenyltrimethoxysilane, 193 g of "Optolake" TR-527 with a number average particle diameter of 15 nm (commercial name, produced by Catalysts & Chemicals Industries Co., Ltd., composition: 20% by weight of titanium oxide particles and 80% by weight of methanol), and 94.0 g of propylene glycol monomethyl ether acetate, and to the resulting solution were added dropwise 16.2 g of water and 0.27 g of phosphoric acid under stirring in such a manner that the reaction temperature would not exceed 40° C. After the adding, a distillation apparatus was attached to a flask, and the resulting solution was heated and stirred at a bath temperature of 105° C. for 2.5 hours, thereby being reacted under evaporation of methanol generated by hydrolysis. Then, the solution was further heated and stirred at a bath temperature of 115° C. for 2 hours and then cooled to room temperature, so that a polymer solution F (with a solid concentration of 44% by weight) was obtained. A 20-gram portion of the resulting polymer solution F was taken, and 0.352 g of [[(2-nitrobenzyl) oxy]carbonyl] cyclohexylamine (NCA), which is a photobase generator, 3.96 g of an imidosilane compound (i) solution (with a solid content of 0.792 g), 3.96 g of an imidosilane compound (iii) solution (with a solid content of 0.792 g), 0.044 g of 9,10-dipropoxyanthracene (DPA), which is a sensitizer, and 20 g of propylene glycol monomethyl ether acetate were added and dissolved, so that a siloxane-based resin composition 9 was obtained.

A cured film was prepared by using the resulting siloxane-based resin composition 9, and evaluation was performed with respect to a refractive index, a transmittance, crack resistance, adhesion, and planarization performance by the above-described methods.

Example 10

A siloxane-based resin composition 10 was obtained in the same manner as in Example 9 except for not using NCA and DPA. A cured film was prepared by using the resulting siloxane-based resin composition 10, and evaluation was performed with respect to a refractive index, a transmittance, crack resistance, adhesion, and planarization performance by the above-described methods.

Example 11

Into 20 g of the polymer solution F used in Example 9 were added and dissolved 25 g of propylene glycol monomethyl ether acetate, 1.76 g of an imidosilane compound (iii) solution (with a solid content of 0.352 g), 0.264 g of 2,2-dimethoxybenzyl-4-t-butylphenol (commercial name: DMOM-PTBP, produced by Honshu Chemical Industry Co., Ltd.), which is a crosslinking compound, and 0.088 g of 2-methylbenzyl-4-acetylphenylmethylsulfonium trifluoromethanesulfonate (MBAPMT), which is a thermal acid generator, so that a siloxane-based resin composition 11 was obtained.

A cured film was prepared by using the resulting siloxane-based resin composition 11, and evaluation was performed with respect to a refractive index, a transmittance, crack resistance, adhesion, and planarization performance by the above-described methods.

Example 12

A siloxane-based resin composition 12 was obtained in the same manner as in Example 11 except for not using DMOM-PTBP and MBAPMT. A cured film was prepared by using the resulting siloxane-based resin composition 12, and evaluation was performed with respect to a refractive index, a transmittance, crack resistance, adhesion, and planarization performance by the above-described methods.

Example 13

Into 20 g of the polymer solution F used in Example 9 were added and dissolved 25 g of propylene glycol monomethyl ether acetate, 1.76 g of an imidosilane compound (iii) solution (with a solid content of 0.352 g), 2.64 g of S-3, which is a crosslinking compound, and 0.0176 g of benzyl-4-hydroxyphenylmethylsulfonium trifluoromethanesulfonate (BHPMT), which is a thermal acid generator, so that a siloxane-based resin composition 13 was obtained.

A cured film was prepared by using the resulting siloxane-based resin composition 13, and evaluation was performed with respect to a refractive index, a transmittance, crack resistance, adhesion, and planarization performance by the above-described methods.

Example 14

A siloxane-based resin composition 14 was obtained in the same manner as in Example 13 except for not using S-3. A cured film was prepared by using the resulting siloxane-based resin composition 14, and evaluation was performed with respect to a refractive index, a transmittance, crack resistance, adhesion, and planarization performance by the above-described methods.

Example 15

Into 20 g of the polymer solution F used in Example 9 were added and dissolved 25 g of propylene glycol monomethyl ether acetate, 1.76 g of an imidosilane compound (iii) solution (with a solid content of 0.352 g), 0.88 g of "NIKALAC" MX-270 (produced by SANWA CHEMICAL CO., LTD.), which is a crosslinking compound, and 0.176 g of 1-methyl-1-(4-biphenylyl)ethyl carbamate (MBEC), which is a thermal base generator, so that a siloxane-based resin composition 15 was obtained.

A cured film was prepared by using the resulting siloxane-based resin composition 15, and evaluation was performed with respect to a refractive index, a transmittance, crack resistance, adhesion, and planarization performance by the above-described methods.

Example 16

A siloxane-based resin composition 16 was obtained in the same manner as in Example 15 except for not using MBEC. A cured film was prepared by using the resulting siloxane-based resin composition 16, and evaluation was performed with respect to a refractive index, a transmittance, crack resistance, adhesion, and planarization performance by the above-described methods.

Example 17

Into 20 g of the polymer solution F used in Example 9 were added and dissolved 25 g of propylene glycol monomethyl ether acetate, 1.76 g of an imidosilane compound (iii) solution (with a solid content of 0.352 g), 1.32 g of TML-BPA (produced by Honshu Chemical Industry Co., Ltd.), which is a crosslinking compound, and 0.44 g of benzyl-4-hydroxyphenylmethylsulfonium trifluoromethanesulfonate (BHPMT), which is a thermal acid generator, so that a siloxane-based resin composition 17 was obtained.

A cured film was prepared by using the resulting siloxane-based resin composition 17, and evaluation was performed with respect to a refractive index, a transmittance, crack resistance, adhesion, and planarization performance by the above-described methods.

Example 18

Into a reaction vessel were charged 24.5 g (0.18 mol) of methyltrimethoxysilane, 83.3 g (0.42 mol) of phenyl trimethoxysilane, and 124.0 g of γ-butyrolactone, and 38 g of water and 0.57 g of phosphoric acid were added dropwise under stirring in such a manner that the reaction temperature would not exceed 30° C. After the adding, a distillation apparatus was attached to a flask, and the resulting solution was heated and stirred at a bath temperature of 105° C. for 2.5 hours, thereby being reacted under evaporation of methanol generated by hydrolysis. Then, the solution was further heated and stirred at a bath temperature of 130° C. for 2 hours and then cooled to room temperature, so that a polymer solution G (with a solid concentration of 32% by weight) was obtained. A 10.0-gram portion of the resulting polymer solution G was taken, and 1.92 g (the amount of solid: 0.384 g) of an imidosilane compound (i) solution and propylene glycol monomethyl ether acetate were added thereto and stirred, so that a siloxane-based resin composition 18 was obtained.

Using the resulting siloxane-based resin composition 18, evaluation was performed with respect to a refractive index, a transmittance, crack resistance, adhesion, and planarization performance by the above-described methods.

Example 19

A siloxane-based resin composition 19 was obtained in the same manner as in Example 18 except for changing the amount of the imidosilane compound (i) solution to 0.32 g (with a solid amount of 0.064 g). A cured film was prepared by using the resulting siloxane-based resin composition 19, and evaluation was performed with respect to a refractive index, a transmittance, crack resistance, adhesion, and planarization performance by the above-described methods.

Example 20

Into a reaction vessel were charged 12.3 g (0.15 mol) of methyltrimethoxysilane, 41.6 g (0.35 mol) of phenyltrimethoxysilane, 146.21 g of a silica particle (with a number average particle diameter of 20 nm) dispersion liquid in a diacetone alcohol solvent "QUATRON" PL-2L-DAA (commercial name, produced by FUSO CHEMICAL CO., LTD., with a solid concentration of 26.4% by weight), and 94.0 g of propylene glycol monomethyl ether acetate, and to the resulting solution were added dropwise 16.2 g of water and 0.27 g of phosphoric acid under stirring in such a manner that the reaction temperature would not exceed 40° C. After the adding, a distillation apparatus was attached to a flask, and the resulting solution was heated and stirred at a bath temperature of 105° C. for 2.5 hours, thereby being reacted under evaporation of methanol generated by hydrolysis. Then, the solution was further heated and stirred at a bath temperature of 115° C. for 2 hours and then cooled to room temperature, so that a polymer solution H (with a solid concentration of 44% by weight) was obtained. A 20-gram portion of the resulting polymer solution H was taken, and 3.52 g of S-11 (commercial name: PDS-9931 (produced by Gelest Inc.), which is a crosslinking compound, 2.2 g (the amount of solid: 0.44 g) of an imidosilane compound (iii) solution and 20 g of propylene glycol monomethyl ether acetate were added thereto and dissolved, so that a siloxane-based resin composition 20 was obtained.

A cured film was prepared by using the resulting siloxane-based resin composition 20, and evaluation was performed with respect to a refractive index, a transmittance, crack resistance, adhesion, and planarization performance by the above-described methods.

Example 21

A siloxane-based resin composition 21 was obtained in the same manner as in Example 20 except for not using S-11. A cured film was prepared by using the resulting siloxane-based resin composition 21, and evaluation was performed with respect to a refractive index, a transmittance, crack resistance, adhesion, and planarization performance by the above-described methods.

Example 22

In 280.22 g of propylene glycol monobutyl ether (boiling point: 170° C.) were dissolved 152.67 g (0.7 mol) of trifluoropropyl trimethoxysilane and 70.89 g (0.3 mol) of γ-glycidoxypropyltrimethoxysilane, and then 54.0 g of water and 1.12 g of phosphoric acid were added thereto under stirring. The resulting solution was heated at a bath temperature of 105° C. for 2 hours and thereby the internal temperature was raised to 90° C., so that a component mainly composed of by-product methanol was distilled off. Subsequently, heating was carried out at a bath temperature of 130° C. for 4.0 hours and the internal temperature was raised to 118° C. to distill off a component mainly composed of water and propylene glycol monobutyl ether. Then cooling to room temperature was carried out, so that a polymer solution I (with a solid concentration of 45% by weight) was obtained. A 20-gram portion of the resulting polymer solution I was taken, and 0.9 g (the amount of solid: 0.18 g) of an imidosilane compound (i) solution, 0.18 g of 2-methylbenzyl-4-acetylphenylmethylsulfonium trifluoromethanesulfonate (MBAPMT), which is a thermal acid generator, and 20 g of propylene glycol monomethyl ether acetate were added thereto and dissolved, so that a siloxane-based resin composition 22 was obtained.

A cured film was prepared by using the resulting siloxane-based resin composition 22, and evaluation was performed with respect to a refractive index, a transmittance, crack resistance, adhesion, and planarization performance by the above-described methods.

Example 23

A siloxane-based resin composition 23 was obtained in the same manner as in Example 22 except for not using MBAPMT. A cured film was prepared by using the resulting siloxane-based resin composition 23, and evaluation was performed with respect to a refractive index, a transmittance, crack resistance, adhesion, and planarization performance by the above-described methods.

Example 24

In 471.09 g of propylene glycol monomethyl ether (boiling point: 121° C.) were dissolved 234.05 g (0.5 mol) of tridecafluorooctyl trimethoxysilane and 123.2 g (0.5 mol) of β-(3,4-epoxycyclohexyl)ethyl trimethoxysilane, and then 63.0 g of water and 1.79 g of phosphoric acid were added thereto under stirring. The resulting solution was heated at a bath temperature of 105° C. for 2 hours and thereby the internal temperature was raised to 90° C., so that a component mainly composed of by-product methanol was distilled off. Subsequently, heating was carried out at a bath temperature of 115° C. for 4.0 hours and the internal temperature was raised to 118° C. to distill off a component mainly composed of water and propylene glycol monomethyl ether. Then cooling to room temperature was carried out, so that a polymer solution J (with a solid concentration of 43% by weight) was obtained. A 20-gram portion of the resulting polymer solution J was taken, and 0.9 g (the amount of solid: 0.18 g) of an imidosilane compound (i) solution, 0.18 g of "NIKALAC" MX-280 (produced by SANWA CHEMICAL CO., LTD.), which is a crosslinking compound, and 20 g of propylene glycol monomethyl ether acetate were added thereto and dissolved, so that a siloxane-based resin composition 24 was obtained.

A cured film was prepared by using the resulting siloxane-based resin composition 24, and evaluation was performed with respect to a refractive index, a transmittance, crack resistance, adhesion, and planarization performance by the above-described methods.

Example 25

Into a reaction vessel were charged 32.72 g (0.15 mol) of trifluoropropyltrimethoxysilane, 82.71 g (0.35 mol) of γ-glycidoxypropyltrimethoxysilane, 146.21 g of a silica particle dispersion liquid in a diacetone alcohol solvent "QUATRON" PL-2L-DAA, and 94.0 g of propylene glycol monomethyl ether acetate, and to the resulting solution were added dropwise 16.2 g of water and 0.27 g of phosphoric acid under stirring in such a manner that the reaction temperature would not exceed 40° C. After the adding, a distillation apparatus was attached to a flask, and the resulting solution was heated and stirred at a bath temperature of 105° C. for 2.5 hours, thereby being reacted under evaporation of methanol generated by hydrolysis. Then, the solution was further heated and stirred at a bath temperature of 115° C. for 2 hours and then cooled to room temperature, so that a polymer solution K (with a solid concentration of 44% by weight) was obtained. A 20-gram portion of the resulting polymer solution K was taken, and 0.88 g (the amount of solid: 0.176 g) of an imidosilane compound (i) solution, 0.176 g of α-4-methoxyphenylacetonitrile (commercial name: PAI-106, produced by Midori Kagaku Co., Ltd.), which is a photoacid generator, and 20 g of propylene glycol monomethyl ether acetate were added thereto and dissolved, so that a siloxane-based resin composition 25 was obtained.

A cured film was prepared by using the resulting siloxane-based resin composition 25, and evaluation was performed with respect to a refractive index, a transmittance, crack resistance, adhesion, and planarization performance by the above-described methods.

Example 26

A siloxane-based resin composition 26 was obtained in the same manner as in Example 25 except for not using PAI-106. A cured film was prepared by using the resulting siloxane-based resin composition 26, and evaluation was performed with respect to a refractive index, a transmittance, crack resistance, adhesion, and planarization performance by the above-described methods.

Example 27

A siloxane-based resin composition 27 was obtained in the same manner as in Example 12 except for changing the amount of the imidosilane compound (iii) solution to 9.7 g (with a solid amount of 1.94 g). A cured film was prepared by using the resulting siloxane-based resin composition 27, and evaluation was performed with respect to a refractive index, a transmittance, crack resistance, adhesion, and planarization performance by the above-described methods.

Example 28

A siloxane-based resin composition 28 was obtained in the same manner as in Example 18 except for changing the amount of the imidosilane compound (i) solution to 4.0 g (with a solid amount of 0.8 g). A cured film was prepared by using the resulting siloxane-based resin composition 28, and evaluation was performed with respect to a refractive index, a transmittance, crack resistance, adhesion, and planarization performance by the above-described methods.

Example 29

A siloxane-based resin composition 29 was obtained in the same manner as in Example 23 except for changing the amount of the imidosilane compound (i) solution to 0.036 g (with a solid amount of 0.0072 g). A cured film was prepared by using the resulting siloxane-based resin composition 29, and evaluation was performed with respect to a refractive index, a transmittance, crack resistance, adhesion, and planarization performance by the above-described methods.

Example 30

Into a reaction vessel were charged 20.4 g (0.15 mol) of methyltrimethoxysilane, 39.66 g (0.20 mol) of phenyltrimethoxysilane, 238.09 g of an imodosilane compound (i) solution (the amount of solid: 47.62 g, 0.15 mol), 70.6 g of "Optolake" TR-521 with a number average particle diameter of 15 nm, and 44.1 g of γ-butyrolactone, and to the resulting solution were added dropwise 30.6 g of water and 0.48 g of phosphoric acid under stirring in such a manner that the reaction temperature would not exceed 40° C. After the adding, a distillation apparatus was attached to a flask, and the resulting solution was heated and stirred at a bath temperature of 105° C. for 2.5 hours, thereby being reacted under evaporation of methanol generated by hydrolysis. Then, the solution was further heated and stirred at a bath temperature of 130° C. for 2 hours and then cooled to room temperature, so that a polymer solution L (with a solid concentration of 55% by weight) was obtained. Into 10 g of the resulting polymer solution L was added and dissolved 10 g of γ-butyrolactone, it dissolved, so that a siloxane-based resin composition 30 was obtained.

Using the resulting siloxane-based resin composition 30, evaluation was performed with respect to a refractive index, a transmittance, crack resistance, adhesion, and planarization performance by the above-described methods.

Example 31

Into 10 g of the polymer solution L used in Example 30 were added and dissolved 10 g of γ-butyrolactone and 2.5 g of an imidosilane compound (i) solution (with a solid content of 0.5 g), so that a siloxane-based resin composition 31 was obtained.

Using the resulting siloxane-based resin composition 31, evaluation was performed with respect to a refractive index, a transmittance, crack resistance, adhesion, and planarization performance by the above-described methods.

Example 32

Into a reaction vessel were charged 24.5 g (0.18 mol) of methyltrimethoxysilane, 43.63 g (0.22 mol) of phenyltrimethoxysilane, 339.42 g of an imodosilane compound (II) solution (the amount of solid: 67.88 g, 0.20 mol), and 124.0 g of γ-butyrolactone, and 38 g of water and 0.57 g of phosphoric acid were added dropwise under stirring in such a manner that the reaction temperature would not exceed 30° C. After the adding, a distillation apparatus was attached to a flask, and the resulting solution was heated and stirred at a bath temperature of 105° C. for 2.5 hours, thereby being reacted under evaporation of methanol generated by hydrolysis. Then, the solution was further heated and stirred at a bath temperature of 130° C. for 2 hours and then cooled to room temperature, so that a polymer solution M (with a solid concentration of 32% by weight) was obtained. A 10.0-gram portion of the resulting polymer solution M was taken, and propylene glycol monomethyl ether acetate was added thereto and stirred, so that a siloxane-based resin composition 32 was obtained.

Using the resulting siloxane-based resin composition 32, evaluation was performed with respect to a refractive index, a transmittance, crack resistance, adhesion, and planarization performance by the above-described methods.

Example 33

Into a reaction vessel were charged 24.5 g (0.18 mol) of methyltrimethoxysilane, 43.63 g (0.22 mol) of phenyltrimethoxysilane, 339.42 g of an imodosilane compound (II) solution (the amount of solid: 67.88 g) (0.20 mol), and 124.0 g of γ-butyrolactone, and 38 g of water and 0.57 g of phosphoric acid were added dropwise under stirring in such a manner that the reaction temperature would not exceed 30° C. After the adding, a distillation apparatus was attached to a flask, and the resulting solution was heated and stirred at a bath temperature of 105° C. for 2.5 hours, thereby being reacted under evaporation of methanol generated by hydrolysis. Then, the solution was further heated and stirred at a bath temperature of 130° C. for 2 hours and then cooled to room temperature, so that a polymer solution M (with a solid concentration of 32% by weight) was obtained. A 10.0-gram portion of the resulting polymer solution M was taken, and 1.92 g (the amount of solid: 0.384 g) of an imidosilane compound (i) solution and propylene glycol monomethyl ether acetate were added thereto and stirred, so that a siloxane-based resin composition 33 was obtained.

Using the resulting siloxane-based resin composition 33, evaluation was performed with respect to a refractive index, a transmittance, crack resistance, adhesion, and planarization performance by the above-described methods.

Example 34

In 280.22 g of propylene glycol monobutyl ether (boiling point: 170° C.) were dissolved 152.67 g (0.7 mol) of trifluoropropyl trimethoxysilane, 47.26 g (0.2 mol) of γ-glycidoxypropyltrimethoxysilane, and 139.71 g of an imidosilane compound (II) solution (the amount of solid: 33.94 g, 0.1 mol), and then 54.0 g of water and 1.12 g of phosphoric acid were added thereto under stirring. The resulting solution was heated at a bath temperature of 105° C. for 2 hours and thereby the internal temperature was raised to 90° C., so that a component mainly composed of by-product methanol was distilled off. Subsequently, heating was carried out at a bath temperature of 130° C. for 4.0 hours and the internal temperature was raised to 118° C. to distill off a component mainly composed of water and propylene glycol monobutyl ether. Then cooling to room temperature was carried out, so that a polymer solution N (with a solid concentration of 45% by weight) was obtained. A 20-gram portion of the resulting polymer solution N was taken, and 0.9 g (the amount of solid: 0.18 g) of an imidosilane compound (i) solution, 0.18 g of 2-methylbenzyl-4-acetylphenylmethylsulfonium trifluoromethanesulfonate (MBAPMT), which is a thermal acid generator, and 20 g of propylene glycol monomethyl ether acetate were added thereto and dissolved, so that a siloxane-based resin composition 34 was obtained.

A cured film was prepared by using the resulting siloxane-based resin composition 34, and evaluation was performed with respect to a refractive index, a transmittance, crack resistance, adhesion, and planarization performance by the above-described methods.

Example 35

Into 10 g of the resulting polymer solution A used in Example 1 were added and dissolved 10 g of γ-butyrolactone and 2.5 g of an imidosilane compound (viii) solution (with a solid content of 0.5 g), so that a siloxane-based resin composition 35 was obtained. Using the resulting siloxane-based resin composition 35, evaluation was performed with respect to a refractive index, a transmittance, crack resistance, adhesion, and planarization performance by the above-described methods.

Example 36

A siloxane-based resin composition 36 was obtained in the same manner as in Example 35 except for exchanging the imidosilane compound (viii) to the imidosilane compound (ix). Using the resulting siloxane-based resin composition 36, evaluation was performed with respect to a refractive index, a transmittance, crack resistance, adhesion, and planarization performance by the above-described methods.

Example 37

A siloxane-based resin composition 37 was obtained in the same manner as in Example 35 except for exchanging the imidosilane compound (viii) to the imidosilane compound (x). Using the resulting siloxane-based resin composition 37, evaluation was performed with respect to a refractive index, a transmittance, crack resistance, adhesion, and planarization performance by the above-described methods.

Example 38

A 10.0-gram portion of the polymer solution M used in Example 33 was taken, and 1.92 g (the amount of solid: 0.384 g) of an imidosilane compound (viii) solution and propylene glycol monomethyl ether acetate were added thereto and stirred, so that a siloxane-based resin composition 38 was obtained. Using the resulting siloxane-based resin composition 38, evaluation was performed with respect to a refractive index, a transmittance, crack resistance, adhesion, and planarization performance by the above-described methods.

Example 39

A 10.0-gram portion of the polymer solution M used in Example 33 was taken, and 1.92 g (the amount of solid: 0.384 g) of an imidosilane compound (viii) solution and propylene glycol monomethyl ether acetate were added thereto and stirred, so that a siloxane-based resin composition 39 was obtained. Using the resulting siloxane-based resin composition 39, evaluation was performed with respect to a refractive index, a transmittance, crack resistance, adhesion, and planarization performance by the above-described methods.

Comparative Example 1

A siloxane-based resin composition A1 was obtained in the same manner as in Example 1 except for not using the imidosilane compound (i). A cured film was prepared by using the resulting siloxane-based resin composition A1, and evaluation was performed with respect to a refractive index, a transmittance, crack resistance, adhesion, and planarization performance by the above-described methods.

Comparative Example 2

A siloxane-based resin composition A2 was obtained in the same manner as in Example 4 except for not using the imidosilane compound (i). A cured film was prepared by using the resulting siloxane-based resin composition A2, and evaluation was performed with respect to a refractive index, a transmittance, crack resistance, adhesion, and planarization performance by the above-described methods.

Comparative Example 3

A siloxane-based resin composition A3 was obtained in the same manner as in Example 5 except for not using the imidosilane compound (i). A cured film was prepared by using the resulting siloxane-based resin composition A3, and evaluation was performed with respect to a refractive index, a transmittance, crack resistance, adhesion, and planarization performance by the above-described methods.

Comparative Example 4

A siloxane-based resin composition A4 was obtained in the same manner as in Example 7 except for not using the imidosilane compound (II). A cured film was prepared by using the resulting siloxane-based resin composition A4, and evaluation was performed with respect to a refractive index, a transmittance, crack resistance, adhesion, and planarization performance by the above-described methods.

Comparative Example 5

A siloxane-based resin composition A5 was obtained in the same manner as in Example 15 except for not using the imidosilane compound (iii). A cured film was prepared by using the resulting siloxane-based resin composition A5, and evaluation was performed with respect to a refractive index, a transmittance, crack resistance, adhesion, and planarization performance by the above-described methods.

Comparative Example 6

A siloxane-based resin composition A6 was obtained in the same manner as in Example 18 except for not using the imidosilane compound (i). A cured film was prepared by using the resulting siloxane-based resin composition A6, and evaluation was performed with respect to a refractive index, a transmittance, crack resistance, adhesion, and planarization performance by the above-described methods.

Comparative Example 7

A siloxane-based resin composition A7 was obtained in the same manner as in Example 22 except for not using the imidosilane compound (i). A cured film was prepared by using the resulting siloxane-based resin composition A7, and evaluation was performed with respect to a refractive index, a transmittance, crack resistance, adhesion, and planarization performance by the above-described methods.

Comparative Example 8

A siloxane-based resin composition A8 was obtained in the same manner as in Example 24 except for not using the imidosilane compound (i). A cured film was prepared by using the resulting siloxane-based resin composition A8, and evaluation was performed with respect to a refractive index, a transmittance, crack resistance, adhesion, and planarization performance by the above-described methods.

Comparative Example 9

A siloxane-based resin composition A9 was obtained in the same manner as in Example 25 except for not using the imidosilane compound (i). A cured film was prepared by using the resulting siloxane-based resin composition A9, and evaluation was performed with respect to a refractive index, a transmittance, crack resistance, adhesion, and planarization performance by the above-described methods.

Comparative Example 10

A siloxane-based resin composition A10 was obtained in the same manner as in Example 1 except for exchanging the imidosilane compound (iv) to the imidosilane compound (i). A cured film was prepared by using the resulting siloxane-based resin composition A10, and evaluation was performed with respect to a refractive index, a transmittance, crack resistance, adhesion, and planarization performance by the above-described methods.

Comparative Example 11

A siloxane-based resin composition A11 was obtained in the same manner as in Example 11 except for exchanging the imidosilane compound (iii) to the imidosilane compound (v). A cured film was prepared by using the resulting siloxane-based resin composition A11, and evaluation was performed with respect to a refractive index, a transmittance, crack resistance, adhesion, and planarization performance by the above-described methods.

Comparative Example 12

A siloxane-based resin composition A12 was obtained in the same manner as in Example 18 except for exchanging the imidosilane compound (i) to the aromatic bisimide oligomer (vi). A cured film was prepared by using the resulting siloxane-based resin composition A12, and evaluation was performed with respect to a refractive index, a transmittance, crack resistance, adhesion, and planarization performance by the above-described methods.

Comparative Example 13

A siloxane-based resin composition A13 was obtained in the same manner as in Example 25 except for exchanging the imidosilane compound (i) to the silicone polyimide precursor (vii). A cured film was prepared by using the resulting siloxane-based resin composition A13, and evaluation was performed with respect to a refractive index, a transmittance, crack resistance, adhesion, and planarization performance by the above-described methods.

Comparative Example 14

To a 2-L separable flask fitted with a cooling tube and a stirring device were added 172.8 g (1.6 mol) of m-cresol, 36.6 g (0.3 mol) of 2,3-dimethylphenol, 12.2 g (0.1 mol) of 3,4-dimethylphenol, 12.6 g of an 37% by weight aqueous formaldehyde solution (formaldehyde: 1.5 mol), 12.6 g (0.1 mol) of oxalic acid dihydrate, and 554 g of methyl isobutyl ketone, which were stirred for 30 minutes and then left at rest for 1 hour. Of two separate layers, the upper layer was removed by decantation, and ethyl 2-hydroxypropionate (HPE) was added. Then, residual methyl isobutyl ketone and water were removed by reduced pressure concentration, so that an HPE resin solution was obtained. HPE was further added to the resulting HPE resin solution, so that a novolac resin solution (with a solid concentration of 43% by weight) was obtained. A 20-gram portion of the resulting novolac resin solution was taken, and 0.77 g of an imidosilane compound (i), 0.172 g of α-4-methoxyphenylacetonitrile (commercial name: PAI-106, produced by Midori Kagaku Co., Ltd.), which is a photoacid generator, and 20 g of propylene glycol monomethyl ether acetate were added thereto and dissolved, so that a novolac-based resin composition B1 was obtained.

A cured film was prepared by using the resulting novolac-based resin composition B1, and evaluation was performed with respect to a refractive index, a transmittance, crack resistance, adhesion, and planarization performance by the above-described methods.

Comparative Example 15

Into a 500-mL three-neck flask were charged 5 g of 2,2-azobis(2,4-dimethylvaleronitrile) and 200 g of diethylene glycol ethyl methyl ether (EDM). Subsequently, 25 g of styrene, 20 g of methacrylic acid, 45 g of glycidyl methacrylate, and 10 g of tricyclo[5.2.1.02,6]decan-8-yl methacrylate were charged. After stirring at room temperature for 30 minutes, the atmosphere in the flask was replaced with nitrogen. Then, the flask was soaked in an oil bath of 70° C., and heating and stirring were conducted for 5 hours. To the resulting EDM solution was further added EDM, so that an acrylic resin solution (with a solid concentration of 43% by weight) was obtained. The weight average molecular weight (Mw) of the resulting acrylic polymer was 15000. A 20-gram portion of the resulting acrylic resin solution was taken, and 0.77 g of an imidosilane compound (ii), 0.258 g of "NIKALAC" MX-270, which is a crosslinking compound, and 20 g of propylene glycol monomethyl ether acetate were added thereto and dissolved, so that an acrylic resin composition B2 was obtained.

A cured film was prepared by using the resulting acrylic resin composition B2, and evaluation was performed with respect to a refractive index, a transmittance, crack resistance, adhesion, and planarization performance by the above-described methods.

The compositions of Examples 1 to 39 and Comparative Examples 1 to 15 are shown in Tables 1 to 4, and evaluation results are shown in Tables 5 to 6.

TABLE 1

| Examples | Composition | (a) Siloxane-based resin | | | (b) Imidosilane compound | Thermally crosslinking agent |
| | | (a) Product (part by weight of solid) | Compound particle (part by weight) | Remarks | (part by weight) | (part by weight) |
| --- | --- | --- | --- | --- | --- | --- |
| Examples 1 | Composition 1 | Polymer solution A 100 | Titanium oxide TR-521 20 | | (i) 9 | — |
| Examples 2 | Composition 2 | Polymer solution B 100 | Titanium oxide TR-521 23 | | (ii) 15 | MX-270 5 |
| Examples 3 | Composition 3 | Polymer solution B 100 | Titanium oxide TR-521 23 | | (ii) 15 | — |
| Examples 4 | Composition 4 | Polymer solution C 100 | Zirconium oxide 23 | | (i) 9 | — |
| Examples 5 | Composition 5 | Polymer solution D 100 | Aluminium oxide 16 | | (i) 9 | — |
| Examples 6 | Composition 6 | Polymer solution D 100 | Aluminium oxide 16 | | (i) 9 | — |
| Examples 7 | Composition 7 | Polymer solution E 100 | Titanium oxide TR-521 18.5 | | (ii) 0.2 | — |
| Examples 8 | Composition 8 | Polymer solution E 100 | Titanium oxide TR-521 18.5 | | (ii) 0.2 | — |
| Examples 9 | Composition 9 | Polymer solution F 100 | Titanium oxide TR-527 42 | | (i)/(iii) 9/9 | — |
| Examples 10 | Composition 10 | Polymer solution F 100 | Titanium oxide TR-527 42 | | (i)/(iii) 9/9 | — |
| Examples 11 | Composition 11 | Polymer solution F 100 | Titanium oxide TR-527 42 | | (iii) 4 | DMOM-PTBP 3 |
| Examples 12 | Composition 12 | Polymer solution F 100 | Titanium oxide TR-527 42 | | (iii) 4 | — |

TABLE 1-continued

| Examples | Composition | (a) Product (part by weight of solid) | Compound particle (part by weight) | | | |
|---|---|---|---|---|---|---|
| Examples 13 | Composition 13 | Polymer solution F 100 | Titanium oxide TR-527 42 | (iii) 4 | S-3 30 | |
| Examples 14 | Composition 14 | Polymer solution F 100 | Titanium oxide TR-527 42 | (iii) 4 | — | |
| Examples 15 | Composition 15 | Polymer solution F 100 | Titanium oxide TR-527 42 | (iii) 4 | MX-270 10 | |
| Examples 16 | Composition 16 | Polymer solution F 100 | Titanium oxide TR-527 42 | (iii) 4 | MX-270 10 | |
| Examples 17 | Composition 17 | Polymer solution F 100 | Titanium oxide TR-527 42 | (iii) 4 | TML-BPA 15 | |

| | Acid generator/base generator (part by weight) | | | | | |
|---|---|---|---|---|---|---|
| Examples | Photoacid generator | Thermal acid generator | Photobase generator | Thermal base generator | Sensitizer (part by weight) | Others (part by weight) |
| Examples 1 | — | — | — | — | — | — |
| Examples 2 | — | — | — | — | — | — |
| Examples 3 | — | — | — | — | — | — |
| Examples 4 | — | — | — | — | — | — |
| Examples 5 | — | BHPMT 3 | — | — | — | — |
| Examples 6 | — | — | — | — | — | — |
| Examples 7 | NDI-101 4 | — | — | — | DBA 0.3 | — |
| Examples 8 | — | — | — | — | — | — |
| Examples 9 | — | — | NCA 4 | — | DPA 0.5 | — |
| Examples 10 | — | — | — | — | — | — |
| Examples 11 | — | MBAPMT 1 | — | — | — | — |
| Examples 12 | — | — | — | — | — | — |
| Examples 13 | — | BHPMT 0.2 | — | — | — | — |
| Examples 14 | — | BHPMT 0.2 | — | — | — | — |
| Examples 15 | — | — | — | MBEC 2 | — | — |
| Examples 16 | — | — | — | — | — | — |
| Examples 17 | — | BHPMT 5 | — | — | — | — |

\* The bottom line indicates the number of parts by weight relative to 100 parts by weight of the solid of (a).

TABLE 2

| Examples | Composition | (a) Siloxane-based resin | | | (b) Imidosilane compound (part by weight) | Thermally crosslinking agent (part by weight) |
|---|---|---|---|---|---|---|
| | | (a) Product (part by weight of solid) | Compound particle (part by weight) | Remarks | | |
| Examples 18 | Composition 18 | Polymer solution G 100 | — | | (i) 12 | — |
| Examples 19 | Composition 19 | Polymer solution G 100 | — | | (i) 2 | — |
| Examples 20 | Composition 20 | Polymer solution H 100 | Silica PL-2L-DAA 42 | | (iii) 5 | S-11 40 |
| Examples 21 | Composition 21 | Polymer solution H 100 | Silica PL-2L-DAA 42 | | (iii) 5 | — |
| Examples 22 | Composition 22 | Polymer solution I 100 | — | Containing fluorine | (i) 2 | — |
| Examples 23 | Composition 23 | Polymer solution I 100 | — | Containing fluorine | (i) 2 | — |
| Examples 24 | Composition 24 | Polymer solution J 100 | — | Containing fluorine | (i) 2 | MX-280 2 |
| Examples 25 | Composition 25 | Polymer solution K 100 | Silica PL-2L-DAA 25 | Containing fluorine | (i) 2 | — |
| Examples 26 | Composition 26 | Polymer solution K 100 | Silica PL-2L-DAA 25 | Containing fluorine | (i) 2 | — |
| Examples 27 | Composition 27 | Polymer solution F 100 | Titanium oxide TR-527 42 | | (iii) 22 | — |
| Examples 28 | Composition 28 | Polymer solution G 100 | — | | (i) 25 | — |
| Examples 29 | Composition 29 | Polymer solution I 100 | — | Containing fluorine | (i) 0.08 | — |

TABLE 2-continued

| Examples | Composition | (a) Product (part by weight of solid) | Compound particle (part by weight) | Remarks | (b) Imidosilane compound (part by weight) | Thermally crosslinking agent (part by weight) |
|---|---|---|---|---|---|---|
| Examples 30 | Composition 30 | Polymer solution L 100 | Titanium oxide TR-521 16 | Containing imidosilane compound (i) | — | — |
| Examples 31 | Composition 31 | Polymer solution L 100 | Titanium oxide TR-521 16 | Containing imidosilane compound (i) | (i) 9 | — |
| Examples 32 | Composition 32 | Polymer solution M 100 | — | Containing imidosilane compound (ii) | — | — |
| Examples 33 | Composition 33 | Polymer solution M 100 | — | Containing imidosilane compound (ii) | (i) 12 | — |

| | Acid generator/base generator (part by weight) | | | | | |
|---|---|---|---|---|---|---|
| Examples | Photoacid generator | Thermal acid generator | Photobase generator | Thermal base generator | Sensitizer (part by weight) | Others (part by weight) |
| Examples 18 | — | — | — | — | — | — |
| Examples 19 | — | — | — | — | — | — |
| Examples 20 | — | — | — | — | — | — |
| Examples 21 | — | — | — | — | — | — |
| Examples 22 | — | MBAPMT 2 | — | — | — | — |
| Examples 23 | — | — | — | — | — | — |
| Examples 24 | — | — | — | — | — | — |
| Examples 25 | PAI-106 2 | — | — | — | — | — |
| Examples 26 | — | — | — | — | — | — |
| Examples 27 | — | — | — | — | — | — |
| Examples 28 | — | — | — | — | — | — |
| Examples 29 | — | — | — | — | — | — |
| Examples 30 | — | — | — | — | — | — |
| Examples 31 | — | — | — | — | — | — |
| Examples 32 | — | — | — | — | — | — |
| Examples 33 | — | — | — | — | — | — |

* The bottom line indicates the number of parts by weight relative to 100 parts by weight of the solid of (a).

TABLE 3

| | | (a) Siloxane-based resin | | | (b) Imidosilane compound | Thermally crosslinking agent |
|---|---|---|---|---|---|---|
| Examples | Composition | (a) Product (part by weight of solid) | Compound particle (part by weight) | Remarks | (part by weight) | (part by weight) |
| Examples 34 | Composition 34 | Polymer solution N 100 | — | Containing fluorine and imidosilane compound (ii) | (i) 2 | — |
| Examples 35 | Composition 35 | Polymer solution A 100 | Titanium oxide TR-521 20 | | (viii) 9 | — |
| Examples 36 | Composition 36 | Polymer solution A 100 | Titanium oxide TR-521 20 | | (ix) 9 | — |
| Examples 37 | Composition 37 | Polymer solution A 100 | Titanium oxide TR-521 20 | | (x) 9 | — |
| Examples 38 | Composition 38 | Polymer solution M 100 | — | imidosilane compound (ii) | (viii) 12 | — |
| Examples 39 | Composition 39 | Polymer solution M 100 | — | imidosilane compound (ii) | (x) 12 | — |

| | Acid generator/base generator (part by weight) | | | | | |
|---|---|---|---|---|---|---|
| Examples | Photoacid generator | Thermal acid generator | Photobase generator | Thermal base generator | Sensitizer (part by weight) | Others (part by weight) |
| Examples 34 | — | MBAPMT 2 | — | — | — | — |
| Examples 35 | — | — | — | — | — | — |
| Examples 36 | — | — | — | — | — | — |
| Examples 37 | — | — | — | — | — | — |

TABLE 3-continued

|  |  |  |  |  |  |
|---|---|---|---|---|---|
| Examples 38 | — | — | — | — | — |
| Examples 39 | — | — | — | — | — |

\* The bottom line indicates the number of parts by weight relative to 100 parts by weight of the solid of (a).

TABLE 4

| Examples | Composition | (a) Siloxane-based resin | | | (b) Imidosilane compound (part by weight) | Thermally crosslinking agent (part by weight) |
|---|---|---|---|---|---|---|
| | | (a) Product (part by weight of solid) | Compound particle (part by weight) | Remarks | | |
| Comparative Example 1 | Composition A1 | Polymer solution A 100 | Titanium oxide TR-521 20 | | — | — |
| Comparative Example 2 | Composition A2 | Polymer solution C 100 | Zirconium oxide 23 | | — | — |
| Comparative Example 3 | Composition A3 | Polymer solution D 100 | Aluminium oxide 16 | | — | — |
| Comparative Example 4 | Composition A4 | Polymer solution E 100 | Titanium oxide TR-521 18.5 | | — | — |
| Comparative Example 5 | Composition A5 | Polymer solution F 100 | Titanium oxide TR-527 42 | | — | MX-270 10 |
| Comparative Example 6 | Composition A6 | Polymer solution G 100 | — | | — | — |
| Comparative Example 7 | Composition A7 | Polymer solution I 100 | — | Containing fluorine | — | — |
| Comparative Example 8 | Composition A8 | Polymer solution J 100 | — | Containing fluorine | — | MX-280 2 |
| Comparative Example 9 | Composition A9 | Polymer solution K 100 | Silica PL-2L-DAA 25 | Containing fluorine | — | — |
| Comparative Example 10 | Composition A10 | Polymer solution A 100 | Titanium oxide TR-521 20 | | — | — |
| Comparative Example 11 | Composition A11 | Polymer solution F 100 | Titanium oxide TR-527 42 | | — | DMOM-PTBP 3 |
| Comparative Example 12 | Composition A12 | Polymer solution G 100 | — | | — | — |
| Comparative Example 13 | Composition A13 | Polymer solution K 100 | Silica PL-2L-DAA 25 | Containing fluorine | — | — |
| Comparative Example 14 | Composition B1 | — | — | | (i) 9 | — |
| Comparative Example 15 | Composition B2 | — | — | | (ii) 9 | MX-270 3 |

| Examples | Acid generator/base generator (part by weight) | | | | Sensitizer (part by weight) | Others (part by weight) |
|---|---|---|---|---|---|---|
| | Photoacid generator | Thermal acid generator | Photobase generator | Thermal base generator | | |
| Comparative Example 1 | — | — | — | — | — | — |
| Comparative Example 2 | — | — | — | — | — | — |
| Comparative Example 3 | — | BHPMT 3 | — | — | — | — |
| Comparative Example 4 | NDI-101 4 | — | — | — | DBA 0.3 | — |
| Comparative Example 5 | — | — | — | MBEC 2 | — | — |
| Comparative Example 6 | — | — | — | — | — | — |
| Comparative Example 7 | — | MBAPMT 2 | — | — | — | — |
| Comparative Example 8 | — | — | — | — | — | — |
| Comparative Example 9 | PAI-106 2 | — | — | — | — | — |
| Comparative Example 10 | — | — | — | — | — | Containing imidosilane compound (iv) 9 |
| Comparative Example 11 | — | MBAPMT 1 | — | — | — | Containing imidosilane |

TABLE 4-continued

| | | | | | | |
|---|---|---|---|---|---|---|
| | | | | | | compound (v) 4 |
| Comparative Example 12 | — | — | — | — | — | Aromatic bisimide oligomer (vi) 12 |
| Comparative Example 13 | PAI-106 2 | — | — | — | — | Silicone polyimide precursor (vii) 2 |
| Comparative Example 14 | PAI-106 2 | — | — | — | — | Novolac resin 100 |
| Comparative Example 15 | — | — | — | — | — | Acrylic resin 100 |

\* The bottom line indicates the number of parts by weight relative to 100 parts by weight of the solid of (a).
\*\* In Comparative Examples 14 and 15 indicated are the numbers of parts by weight relative to 100 parts by weight of the novolac resin solid and the acrylic resin solid, respective

TABLE 5

| | | Evaluation results | | | | |
|---|---|---|---|---|---|---|
| | Composition | Refractive index | Transmittance (%) | Crack resitance 1) | Adhesion (the number of remaining squares: squares) | Cure shrinkage ratio (%) |
| Examples 1 | Composition 1 | 1.64 | 99 | 320° C. | 100 | 8 |
| Examples 2 | Composition 2 | 1.64 | 99 | 360° C. | 95 | 5 |
| Examples 3 | Composition 3 | 1.64 | 99 | 340° C. | 95 | 7 |
| Examples 4 | Composition 4 | 1.62 | 99 | 320° C. | 100 | 8 |
| Examples 5 | Composition 5 | 1.58 | 99 | 340° C. | 100 | 10 |
| Examples 6 | Composition 6 | 1.58 | 99 | 320° C. | 100 | 13 |
| Examples 7 | Composition 7 | 1.62 | 98 | 340° C. | 95 | 12 |
| Examples 8 | Composition 8 | 1.62 | 98 | 320° C. | 95 | 14 |
| Examples 9 | Composition 9 | 1.67 | 98 | 340° C. | 100 | 3 |
| Examples 10 | Composition 10 | 1.67 | 98 | 320° C. | 100 | 3 |
| Examples 11 | Composition 11 | 1.68 | 97 | 360° C. | 100 | 5 |
| Examples 12 | Composition 12 | 1.68 | 96 | 320° C. | 100 | 6 |
| Examples 13 | Composition 13 | 1.66 | 99 | 440° C. | 100 | 10 |
| Examples 14 | Composition 14 | 1.66 | 99 | 340° C. | 100 | 5 |
| Examples 15 | Composition 15 | 1.66 | 98 | 380° C. | 100 | 5 |
| Examples 16 | Composition 16 | 1.66 | 98 | 360° C. | 100 | 7 |
| Examples 17 | Composition 17 | 1.66 | 95 | 380° C. | 100 | 5 |
| Examples 18 | Composition 18 | 1.56 | 98 | 360° C. | 100 | 8 |
| Examples 19 | Composition 19 | 1.56 | 99 | 340° C. | 100 | 15 |
| Examples 20 | Composition 20 | 1.54 | 99 | 460° C. | 100 | 12 |
| Examples 21 | Composition 21 | 1.54 | 99 | 340° C. | 100 | 6 |
| Examples 22 | Composition 22 | 1.40 | 99 | 340° C. | 100 | 14 |
| Examples 23 | Composition 23 | 1.40 | 99 | 320° C. | 100 | 14 |
| Examples 24 | Composition 24 | 1.38 | 99 | 360° C. | 100 | 10 |
| Examples 25 | Composition 25 | 1.42 | 99 | 320° C. | 100 | 7 |
| Examples 26 | Composition 26 | 1.42 | 99 | 300° C. | 100 | 8 |
| Examples 27 | Composition 27 | 1.64 | 94 | 340° C. | 100 | 5 |
| Examples 28 | Composition 28 | 1.55 | 93 | 360° C. | 100 | 7 |
| Examples 29 | Composition 29 | 1.40 | 99 | 320° C. | 90 | 16 |

1) The highest temperature at which cracks generate is indicated

TABLE 6

| | Composition | Refractive index | Transmittance (%) | Crack resitance 1) | Adhesion (the number of remaining squares: squares) | Cure shrinkage ratio (%) |
|---|---|---|---|---|---|---|
| Examples 30 | Composition 30 | 1.64 | 99 | 320° C. | 90 | 10 |
| Examples 31 | Composition 31 | 1.64 | 99 | 360° C. | 100 | 5 |
| Examples 32 | Composition 32 | 1.56 | 98 | 360° C. | 90 | 10 |
| Examples 33 | Composition 33 | 1.56 | 98 | 380° C. | 100 | 5 |
| Examples 34 | Composition 34 | 1.40 | 99 | 360° C. | 100 | 10 |
| Examples 35 | Composition 35 | 1.64 | 99 | 340° C. | 100 | 7 |
| Examples 36 | Composition 36 | 1.64 | 99 | 340° C. | 100 | 6 |
| Examples 37 | Composition 37 | 1.64 | 98 | 380° C. | 100 | 5 |
| Examples 38 | Composition 38 | 1.58 | 96 | 400° C. | 100 | 5 |
| Examples 39 | Composition 39 | 1.60 | 96 | 400° C. | 100 | 5 |
| Comparative Example 1 | Composition A1 | 1.64 | 99 | 320° C. | 50 | 10 |
| Comparative Example 2 | Composition A2 | 1.62 | 99 | 320° C. | 50 | 10 |
| Comparative Example 3 | Composition A3 | 1.58 | 99 | 340° C. | 50 | 14 |
| Comparative Example 4 | Composition A4 | 1.62 | 98 | 320° C. | 50 | 16 |
| Comparative Example 5 | Composition A5 | 1.66 | 98 | 340° C. | 50 | 10 |
| Comparative Example 6 | Composition A6 | 1.56 | 98 | 340° C. | 50 | 18 |
| Comparative Example 7 | Composition A7 | 1.40 | 99 | 320° C. | 50 | 17 |
| Comparative Example 8 | Composition A8 | 1.38 | 99 | 320° C. | 50 | 12 |
| Comparative Example 9 | Composition A9 | 1.42 | 99 | 300° C. | 50 | 12 |
| Comparative Example 10 | Composition A10 | 1.63 | 98 | 320° C. | 80 | 8 |
| Comparative Example 11 | Composition A11 | 1.67 | 97 | 320° C. | 80 | 10 |
| Comparative Example 12 | Composition A12 | 1.55 | 98 | 340° C. | 80 | 20 |
| Comparative Example 13 | Composition A13 | 1.42 | 97 | 320° C. | 80 | 20 |
| Comparative Example 14 | Composition B1 | 1.58 | 90 | 340° C. | 30 | 23 |
| Comparative Example 15 | Composition B2 | 1.54 | 93 | 340° C. | 30 | 25 |

1) The highest temperature at which cracks generate is indicated

INDUSTRIAL APPLICABILITY

A cured film formed from the siloxane-based resin composition of the present invention are used suitably for optical objects, such as an image sensor and an optical filter for a display, such as a liquid crystal display. In more detail, they can be used for a planarization film of an image sensor or an embedding planarization film for waveguides. Moreover, they can be used for low refractive index layers, high refractive index layers, and hard coat layers of antireflection films or antireflection boards of optical filters.

The invention claimed is:

1. A siloxane-based resin composition comprising (a) a siloxane-based resin and (b) an imidosilane compound represented by the following formula (4):

$$\left[ R^{11}-N \begin{array}{c} O \\ \parallel \\ \diagdown \\ \diagup \\ \parallel \\ O \end{array} R^{10} - Si - [R^7]_\alpha \right]_{4-\alpha} \quad (4)$$

wherein in formula (4), $R^7$, which may be the same or different, represents an alkyl group having 1 to 6 carbon atoms, an alkoxyl group having 1 to 6 carbon atoms, a phenyl group, a phenoxy group, or a substituted analogue thereof; $R^{10}$, which may be the same or different, represents a trivalent organic group having 3 to 30 carbon atoms; $R^{11}$, which may be the same or different, represents a hydrogen atom or a silicon atom-free monovalent organic group having 1 to 20 carbon atoms; and α represents an integer of 1 to 3.

2. The siloxane-based resin composition according to claim 1, wherein the siloxane-based resin (a) is (a-1) a reaction product to be obtained by hydrolyzing one or more alkoxysilane compounds each represented by any one of the following formulae (1) to (3) and then making the resulting hydrolysate undergo a condensation reaction:

$$R^1Si(OR^2)_3 \quad (1)$$

wherein in formula (1), $R^1$ represents hydrogen, an alkyl group, an alkenyl group, an aryl group, or a substituted analogue thereof; and $R^2$, which may be the same or different, represents a methyl group, an ethyl group, a propyl group, an isopropyl group, or a butyl group;

$$R^3R^4Si(OR^5)_2 \quad (2)$$

wherein in formula (2), $R^3$ and $R^4$ each represent hydrogen, an alkyl group, an alkenyl group, an aryl group or a substituted analogue thereof; and $R^5$, which may be the same or different, represents a methyl group, an ethyl group, a propyl group, an isopropyl group, or a butyl group;

$$Si(OR^6)_4 \quad (3)$$

wherein in formula (3), $R^6$, which may be the same or different, represents a methyl group, an ethyl group, a propyl group, an isopropyl group, or a butyl group.

3. The siloxane-based resin composition according to claim 2, wherein the reaction product (a-1) is a reaction product to be obtained by hydrolyzing one or more alkoxysilane compounds each represented by any one of the following formulae (1) to (3) in the presence of at least one kind of compound particles selected from the group consisting of silicon compound particles, aluminum compound particles, tin compound particles, titanium compound particles, and zirconium compound particles and then making the resulting hydrolysate undergo a condensation reaction.

4. The siloxane-based resin composition according to claim 1, wherein the siloxane-based resin (a) contains fluorine.

5. The siloxane-based resin composition according to claim 1 which contains (c) an acid generator or a base generator.

6. A material for image sensors which comprises the siloxane-based resin composition according to claim 1.

7. A cured film material obtained by curing the siloxane-based resin composition according to claim 1.

8. An optical object comprising the cured film according to claim 7.

9. An image sensor comprising the cured film according to claim 7.

10. The siloxane-based resin composition according to claim 1, further comprising (d) a crosslinking compound and/or a crosslinking compound represented by the following formula (8):

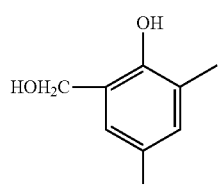
46DMOC

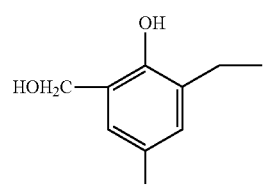
46DMOEP

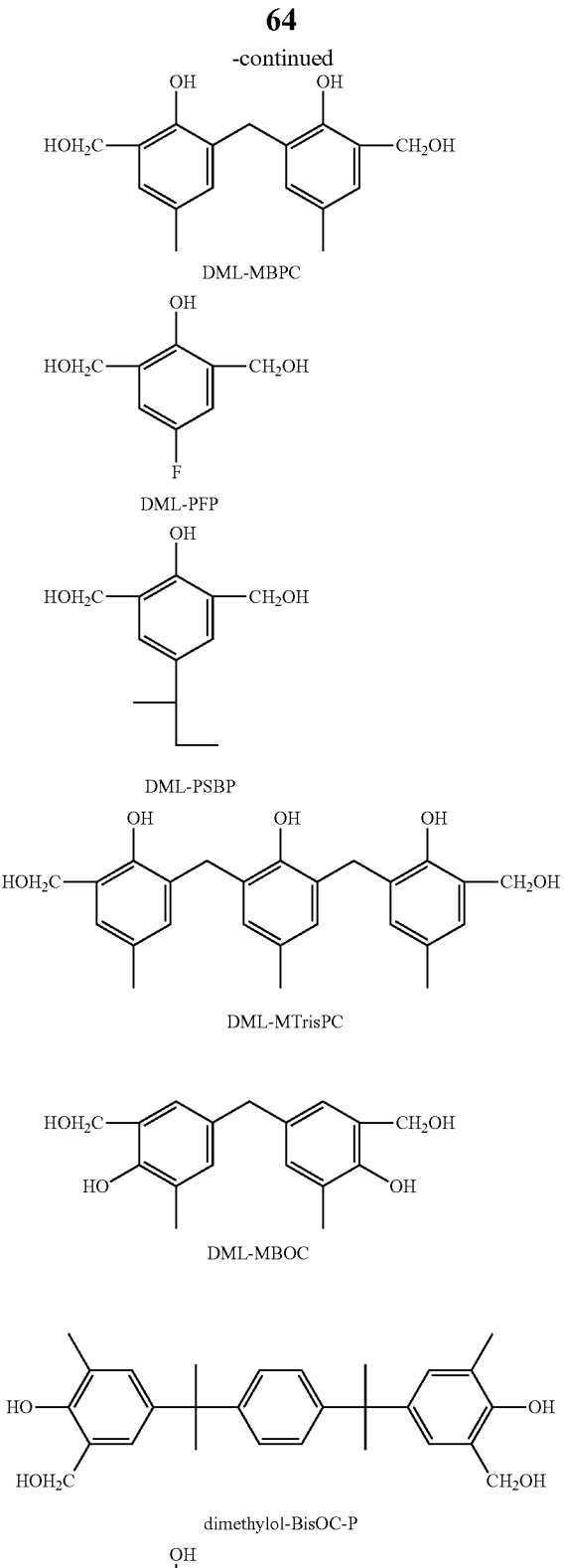

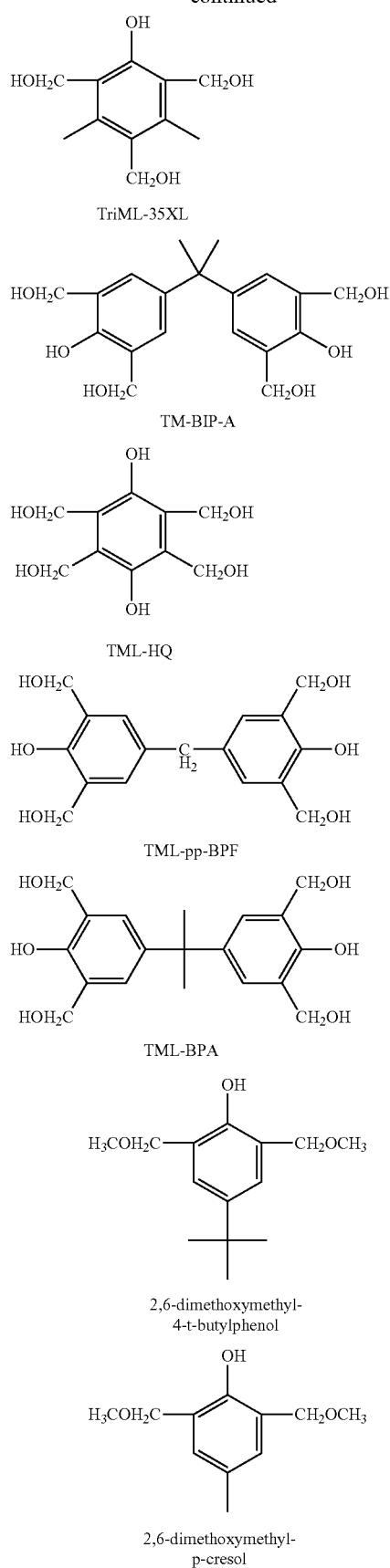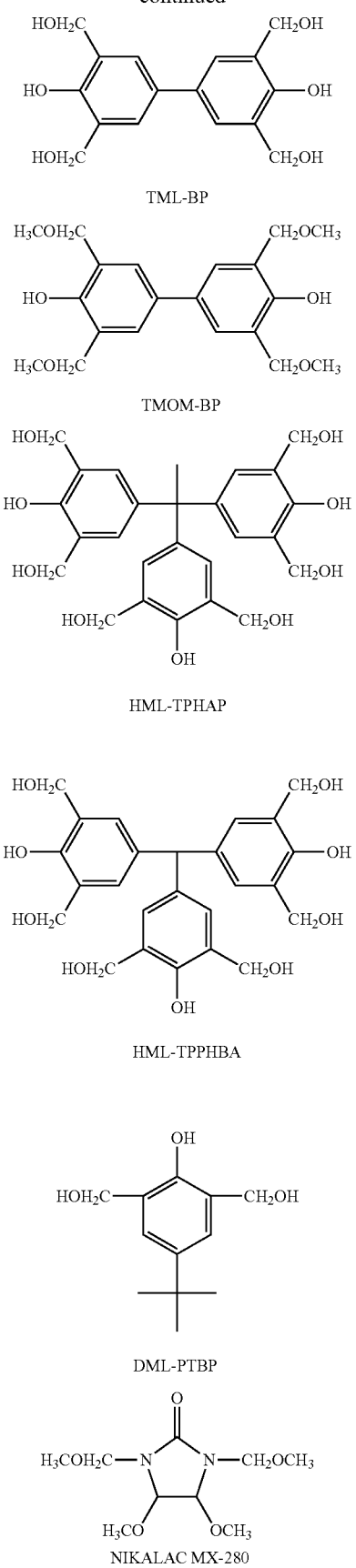

-continued

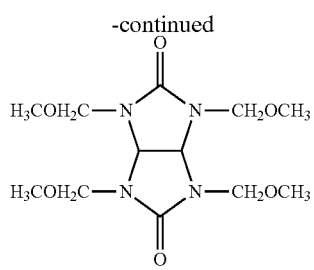

NIKALAC MX-270

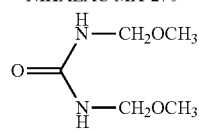

NIKALAC MX-290

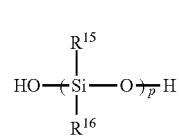
(8)

wherein in formula (8), $R^{15}$ and $R^{16}$, which each may be the same or different, each represent an alkyl group having 1 to 4 carbon atoms, a phenyl group, or a substituted analogue thereof, provided that at least one of p $R^{15}$ and $R^{16}$ are a phenyl group or its substituted analogue.

11. An adhesion improving agent comprising an imidosilane compound represented by the following formula (4):

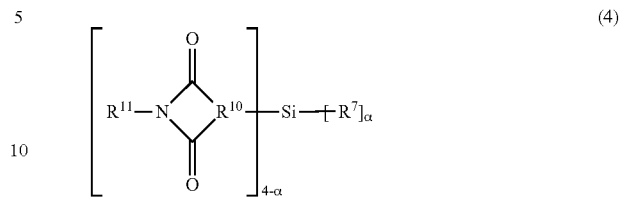

wherein in formula (4), $R^7$, which may be the same or different, represents an alkyl group having 1 to 6 carbon atoms, an alkoxyl group having 1 to 6 carbon atoms, a phenyl group, a phenoxy group;

$R^{10}$, which may be the same or different, represents a trivalent organic group having 3 to 30 carbon atoms;

$R^{11}$, which may be the same or different, represents a hydrogen atom or a silicon atom-free monovalent organic group selected from methyl, ethyl, n-propyl, isopropyl, n-butyl, t-butyl, cyclohexyl, 2-hydroxyethyl, phenyl, methoxyphenyl group, methoxy, ethoxy, n-propoxy, and isopropoxy; and α represents an integer of 1 to 3.

* * * * *